(12) United States Patent
Wargent

(10) Patent No.: US 12,180,496 B2
(45) Date of Patent: Dec. 31, 2024

(54) METHOD TO IMPROVE CROP YIELD AND/OR QUALITY

(71) Applicant: Biolumic Limited, Palmerston North (NZ)

(72) Inventor: Jason John Wargent, Palmerston North (NZ)

(73) Assignee: BIOLUMIC LIMITED, Palmerston North (NZ)

( * ) Notice: Subject to any disclaimer, the term of this patent is extended or adjusted under 35 U.S.C. 154(b) by 0 days.

(21) Appl. No.: 16/727,752

(22) Filed: Dec. 26, 2019

(65) Prior Publication Data

US 2020/0149060 A1 May 14, 2020

Related U.S. Application Data

(63) Continuation of application No. PCT/IB2018/000839, filed on Jun. 29, 2018.

(60) Provisional application No. 62/526,922, filed on Jun. 29, 2017.

(51) Int. Cl.
*C12N 15/82* (2006.01)

(52) U.S. Cl.
CPC ................. *C12N 15/8273* (2013.01)

(58) Field of Classification Search
None
See application file for complete search history.

(56) References Cited

U.S. PATENT DOCUMENTS

| | | |
|---|---|---|
| 4,943,674 A | 7/1990 | Houck et al. |
| 4,987,071 A | 1/1991 | Cech et al. |
| 5,040,329 A | 8/1991 | Michaloski |
| 5,159,135 A | 10/1992 | Umbeck |
| 5,231,020 A | 7/1993 | Jorgensen et al. |
| 5,268,526 A | 12/1993 | Hershey et al. |
| 5,510,471 A | 4/1996 | Lebrun et al. |
| 5,538,880 A | 7/1996 | Lundquist et al. |
| 5,545,508 A | 8/1996 | Marchesano et al. |
| 5,571,706 A | 11/1996 | Baker et al. |
| 5,583,021 A | 12/1996 | Dougherty et al. |
| 5,589,615 A | 12/1996 | De Clercq et al. |
| 5,597,945 A | 1/1997 | Jaynes et al. |
| 5,610,042 A | 3/1997 | Chang et al. |
| 5,677,175 A | 10/1997 | Hodges et al. |
| 5,736,369 A | 4/1998 | Bowen et al. |
| 5,744,693 A | 4/1998 | Meyerowitz et al. |
| 5,750,341 A | 5/1998 | Macevicz |
| 5,750,386 A | 5/1998 | Conkling et al. |
| 5,750,871 A | 5/1998 | Moloney et al. |
| 5,773,269 A | 6/1998 | Somers et al. |
| 5,773,697 A | 6/1998 | Tomes et al. |
| 5,780,708 A | 7/1998 | Lundquist et al. |
| 5,783,393 A | 7/1998 | Kellogg et al. |
| 5,792,929 A | 8/1998 | Mariani et al. |
| 6,306,597 B1 | 10/2001 | Macevicz |
| 6,875,857 B2 | 4/2005 | Simms |
| 7,115,400 B1 | 10/2006 | Adessi et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,348,475 B2 | 3/2008 | Shin et al. |
| 7,948,015 B2 | 5/2011 | Rothberg et al. |
| 8,001,722 B2 | 8/2011 | Wilson et al. |
| 8,845,149 B2 | 9/2014 | Cheng et al. |
| 8,898,818 B1 | 12/2014 | Whitcomb |
| 10,517,225 B2 * | 12/2019 | Wargent ................. A01G 7/045 |
| 10,721,875 B2 * | 7/2020 | Wargent ................... A01G 9/20 |
| 10,750,691 B2 * | 8/2020 | Wargent ................. A01G 22/00 |
| 2006/0016125 A1 | 1/2006 | Krauss et al. |
| 2008/0120736 A1 | 5/2008 | Hurst |
| 2008/0160580 A1 | 7/2008 | Adessi et al. |
| 2008/0286795 A1 | 11/2008 | Kawashima et al. |
| 2008/0298052 A1 | 12/2008 | Hurst et al. |
| 2009/0272029 A1 | 11/2009 | Aiking et al. |
| 2010/0193707 A1 | 8/2010 | Yamada et al. |
| 2011/0163246 A1 | 7/2011 | Ishiwata et al. |
| 2012/0054061 A1 | 3/2012 | Fok et al. |
| 2013/0008085 A1 | 1/2013 | Aikala et al. |
| 2013/0294065 A1 | 11/2013 | Wells |
| 2014/0204567 A1 | 7/2014 | Cheng et al. |
| 2014/0273235 A1 | 9/2014 | Voytas et al. |
| 2015/0167053 A1 | 6/2015 | Mertz, Jr. et al. |

(Continued)

FOREIGN PATENT DOCUMENTS

| | | |
|---|---|---|
| CN | 1447646 A | 10/2003 |
| CN | 101909425 A | 12/2010 |

(Continued)

OTHER PUBLICATIONS

Pang and Hays. "UV-B-Inducible and Temperature-Sensitive Photoreactivation of Cyclobutane Pyrimidine Dimers in *Arabidopsis thaliana*". Plant Physiology. 536-543. (Year: 1991).*
Gaska, et al. "Post-Harvest Produce Preservation using Deep UV LED Technology" Biotech, Biomaterials and Biomedical. TechConnect Briefs: 9-12. (Year: 2016).*
Oliveira et al. "Preharvest UV-C radiation influences physiological, biochemical, and transcriptional changes in strawberry cv. Camarosa". Plant Physiology and Biochemistry. 108: 391-399. (Year: 2016).*
Cechin et al. "Sensitivity of yellow passion fruit to ultraviolet-B radiation". Plant Physiology. 47(10) 1422-1427. (Year: 2012).*
Janisiewicz et al. "Use of low-dose UV-C irradiation to control powdery mildew caused by *Podosphaera aphanis* on strawberry plants". Canadian Journal of Plant Pathology. 38(4) 430-439. 2016 (Year: 2016).*
Kagani et al. Agricultural and Forest Meteorology. 120:191-218. (Year: 2003).*
Behn, H. et al. Development-dependent UV-B Responses in Red Oak Leaf Lettuce (*Lactuca sativa* L.): Physiological Mechanisms and Significance for Hardening, European Journal of Horticultural Science vol. 76, No. 2, pp. 33-40( Jul. 2011) .

(Continued)

*Primary Examiner* — Matthew R Keogh
*Assistant Examiner* — David R Byrnes
(74) *Attorney, Agent, or Firm* — Wilson Sonsini Goodrich & Rosati

(57) ABSTRACT

Provided herein are methods and compositions relating to administering light enriched for UV-B to a plant material to improve subsequent plant performance.

11 Claims, 2 Drawing Sheets

(56) References Cited

U.S. PATENT DOCUMENTS

| | | | |
|---|---|---|---|
| 2016/0073599 A1* | 3/2016 | Wargent | A01G 7/00 800/276 |
| 2016/0184237 A1 | 6/2016 | Lowe et al. | |
| 2016/0345512 A1 | 12/2016 | Wargent | |
| 2017/0000041 A1 | 1/2017 | Wargent | |
| 2019/0183034 A1* | 6/2019 | Wargent | A01C 21/00 |
| 2020/0190532 A1 | 6/2020 | Wargent et al. | |
| 2021/0298243 A1 | 9/2021 | Smith et al. | |
| 2021/0345572 A1 | 11/2021 | Wargent et al. | |
| 2024/0175044 A1 | 5/2024 | Wargent et al. | |

FOREIGN PATENT DOCUMENTS

| | | |
|---|---|---|
| CN | 102149272 A | 8/2011 |
| CN | 103194453 A | 7/2013 |
| CN | 103209582 A | 7/2013 |
| CN | 103476243 A | 12/2013 |
| CN | 103999748 A | 8/2014 |
| CN | 106413378 A | 2/2017 |
| DE | 19900616 A1 | 7/2000 |
| EP | 0007459 A1 | 2/1980 |
| EP | 1300066 A1 | 4/2003 |
| EP | 2172097 A1 | 4/2010 |
| EP | 3143869 A1 | 3/2017 |
| JP | 2001028947 A | 2/2001 |
| JP | 2003339236 A | 12/2003 |
| JP | 2004166638 A | 6/2004 |
| JP | 2005328734 A | 12/2005 |
| JP | 2006158262 A | 6/2006 |
| JP | 2007068512 A | 3/2007 |
| JP | 2010094109 A | 4/2010 |
| JP | 2012183014 A | 9/2012 |
| JP | 2013051939 A | 3/2013 |
| JP | 2013153691 A | 8/2013 |
| JP | 2014233247 A | 12/2014 |
| JP | 2016007185 A | 1/2016 |
| JP | 2017506905 A | 3/2017 |
| KR | 100944359 B1 | 3/2010 |
| NZ | 702063 A | 11/2016 |
| TW | M458082 U | 8/2013 |
| WO | WO-0051414 A1 | 9/2000 |
| WO | WO-2012040838 A1 | 4/2012 |
| WO | WO-2012085336 A1 | 6/2012 |
| WO | WO-2015119510 A1 | 8/2015 |
| WO | WO-2015137825 A1 | 9/2015 |
| WO | WO-2016043605 A1 | 3/2016 |
| WO | WO-2016054268 A1 | 4/2016 |
| WO | WO-2018037281 A1 | 3/2018 |
| WO | WO-2019002946 A1 | 1/2019 |
| WO | WO-2019038594 A2 | 2/2019 |
| WO | WO-2020095117 A2 | 5/2020 |

OTHER PUBLICATIONS

Besteriro et al. Arabidopsis MAP kinase phosphatase 1 and its target MAP kinases 3 and 6 antagonistically determine UV-B stress tolerance, independent of the UVR8 photoreceptor pathway. Plant Journal 58:727-737 (2011).

Chen et al. Shoot-to-Root Mobile Transcription Factor HY5 Coordinates Plant Carbon and Nitrogen Acquisition. Curr Biol 26(5):640-646 (Mar. 2016).

Cluis e tal. The Arabidopsis transcription factor HY5 integrates light and hormone signaling pathways. Plant J 38(2):332-347 (2004).

Davey, M.P. et al. The UV-B photoreceptor UVR8 promotes photosynthetic efficiency in Arabidopsis thaliana exposed to elevated levels of UV-B, Photosynthesis Research, 2012, vol. 114, pp. 121-131.

Ebisawa et al. Supplementary ultraviolet radiation B together with blue light at night increased quercetin content and flavonol synthase gene expression in leaf lettuce (Lactuca sativa L.). Environmental Control In Biology 46(1): 1-11 (2008).

European Application No. 15761440.5 Extended European Search Report Mailed Sep. 19, 2017.

European Appication No. 15841342 Search Report and Opinion Mailed Feb. 13, 2018.

European Patent Application No. EP15746659.0 Extended European Search Report Mailed Oct. 11, 2017.

Favory et al. Interaction of COP1 and UVR8 regulates UV-B-induced photomorphogenesis and stress acclimation in Arabidopsis, Embo Journal, 28(5); 591-601 (2009).

Folta et al. Light as a Growth Regulator: Controlling Plant Biology with Narrow-bandwidth Solid-state Lighting Systems. Hortscience 43:1957-1964 (2008).

Gangappa et al. The Multifaceted Roles of HY5 in Plant Growth and Development. Mol Plant 9(10): 1353-1365 (Oct. 2016).

Heil et al. Induced systemic resistance (ISR) against pathogens—a promising field for ecological research, Perspectives in Plant Ecology, Evolution and Systematics, vol. 4, 2001, pp. 65-79.

Huche-Thelier et al. Light signaling and plant responses to blue and UV radiations—Perspectives for applications in horticulture. Environmental And Experimental Botany, Elsevier, Amsterdam, NL 121:22-38 (2015).

IARC Monographs on the Evaluation of Carcinogenic Risks to Humans. vol. 55—Solar and ultraviolet radiation; Chapter 1; Exposure data (1992) (International Agency for Research on Cancer—World Health Organization).

Ibdah et al. Spectral dependence of flavonol and betacyanin accumulation in Mesembryanthemum crystallinum under enhanced ultraviolet radiation, Plant, Cell and Environment 25: 1145-1154 (2002).

International Application No. PCT/IB2017/001152 International Search Report and Written Opinion Mailed Nov. 8, 2017.

International Application No. PCT/IB2018/000839 International Search Report and Written Opinion dated Oct. 19, 2018.

International Application No. PCT/IB2018/001056 International Search Report and Written Opinion dated Apr. 3, 2019.

International Application No. PCT/NZ2015/000008 International Preliminary Report on Patentability Mailed Apr. 19, 2016.

International Application No. PCT/NZ2015/000008 Written Opinion Mailed Jan. 14, 2016.

International Application No. PCT/NZ2015/000014 International Preliminary Report on Patentability Mailed Nov. 16, 2015.

International Application No. PCT/NZ2015/000014 Written Opinion Mailed Jun. 3, 2015.

International Application No. PCT/NZ2015/050153 International Search Report Mailed Nov. 23, 2015.

International Application No. PCT/NZ2015/050153 Written Opinion Mailed Feb. 18, 2016.

Jansen. Low threshold levels of ultraviolet-B in a background of photosynthetically active radiation trigger rapid degradation of the D2 protein of photosystem—II. The Plant Journal 9(5):693-699 (1996).

Jenkins, G.I. Signal Transduction in Responses to UV-B Radiation, Annual Review of Plant Biology, vol. 60, 2009, pp. 407-431.

Kakani, VG et al. Field crop responses to ultraviolet-B radiation: a review. Agricultural and Forest Meteorology, 120(1-4): 191-218 (Dec. 24, 2003).

Kreft et al., Rutin in buckwheat herbs grown at different UV-B radiation levels: comparison of two UV spectrophotometric and an HPLC method. Journal of Experimental Botany. 53(375):1801-1804 (2002).

Kubasek, W.L. et al. Regulation of flavonoid biosynthetic genes in germinating Arabidopsis seedlings, The Plant Cell, 1992, vol. 4, pp. 1229-1236.

Lee et al. Analysis of transcription factor HY5 genomic binding sites revealed its hierarchical role in light regulation of development. Plant Cell 19(3):731-749 (2007).

Li, X. et al. Effect of UV-B irradiation on seed germination and seedling growth of Arabidopsis, Chinese Bulletin of Botany, 2013, vol. 48, pp. 52-58.

Liu, Bing et al. Effects of enhanced UV-B radiation on seed growth characteristics and yield components in soybean. Field Crops Research, 154:158-163 (2013).

Lydon et al. UV-B Radiation Effects On Photosynthesis. Growth And Cannabinoid Production Of Two Cannabis Sativa Chemotypes. Photochemistry And Photobiology 46(2):201-206 (1987).

(56) References Cited

OTHER PUBLICATIONS

Marzocca, A. et al. Tratamiento de semillas de 'Kok-saghyz' con rayos ultravioletas, Revista de Investigaciones Agrícolas, 1957, vol. XI, pp. 227-245.
Mishra, A. et al. Effect of UVB radiation on seed germination, seedling growth, photosynthetic pigments and biochemical responses of *Postum sativum* (L.). Photosynthetic Pigments and Biochemical Responses of *Pistum Sativum* (L.) Zenith International Journal of Multidisciplinary Research, vol. 5(1), pp. 124-129.
Musil et al. Ultraviolet-B Irradiation Of Seeds Affects Photochemical And Reproductive Performance Of The Arid-Environment Ephemeral Dimorphotheca Pluvialis. Environmental and Experimental Botany 34(4):371-378 (1994).
Ozbolt, L. et al. Distribution of selenium and phenolics in buckwheat plants grown from seeds soaked in Se solution and under different levels of UV-B radiation. Food Chemistry 110(3):691-696 (Oct. 1, 2008).
PCT/IB2018/000839 International Preliminary Report on Patentability dated Dec. 31, 2019.
Peykarestan et al., Uv irradiation effects on seed germination and growth, protein content, peroxidase and protease activity in redbean. International Research Journal of Applied and Basic Sciences. 3(1):92-102 (2012).
Qaderi et al. Morphological and physiological responses of canola (*Brassica napus*) siliquas and seeds to UVB and CO2 under controlledenvironment conditions. Environmental and Experimental Botany 60:428-437 (2007).
Rizzini, L. et al. Perception of UV-B by the *Arabidopsis* UVR8 Protein, Science vol. 332, No. 6025; pp. 103-106 (2011).
Rozema, J. et al. UV-B as an environmental factor in plant life: stress and regulation, Trends in Ecology & Evolution, vol. 12, 1997, pp. 22-28.
Setlow. The Wavelengths in Sunlight Effective in Producing Skin Cancer: A Theoretical Analysis. PNAS 71:3363-3366. (1974).
Shaukat, S.S., et al. Effect of Supplemental UV-B Radiation on Germination, Seedling Growth, and Biochemical Responses of Sunflower (*Helianthus annuus* L.). Fuuast Journal of Biology vol. 1, No. 1, pp. 27-33 (2011).
Siddiqui, S. et al. Effect of UV-B radiation on seed germination, plant height, foliage and seed yield of soybean (*Glicine max* L. *Merrill*), Progressive Agriculture, 2005, vol. 7, pp. 42-45.
Sosa-Flores, V. P. et al. Study of morphological and histological changes in melon plants grown from seeds irradiated with UV-B, Journal of Applied Horticulture, Oct.-Dec. 2104, vol. 16, pp. 199-204.
Tegelberg et al., Red : far-red light ratio and UV-B radiation: their effects on leaf phenolics and growth of silver birch seedlings. Plant, Cell & Environment. 27(8): 1005-1013 (2004).
Tepfer et al. Survival of Plant Seeds, Their UV Screens, and nptII DNA for 18 Months Outside the International Space Station. Astrobiology 12:517-528 (2012).
U.S. Appl. No. 14/857,486 Advisory Office Action Mailed Jul. 27, 2018.
U.S. Appl. No. 14/857,486 Non-Final Office Action Mailed Jun. 16, 2017.
U.S. Appl. No. 14/857,486 Final Office Action dated Jan. 13, 2020.
U.S. Appl. No. 15/117,157 Final Office Action dated Sep. 17, 2019.
U.S. Appl. No. 14/857,486 Office Action dated May 16, 2019.
U.S. Appl. No. 15/117,157 Office Action dated Apr. 3, 2019.
U.S. Appl. No. 15/125,698 Office Action dated Apr. 25, 2019.
U.S. Appl. No. 14/857,486 Non-Final Office Action Mailed Apr. 18, 2018.
Vallad et al. Systemic Acquired Resistance and Induced Systemic Resistance in Conventional Agriculture, Crop Science, vol. 44, Nov.-Dec. 2004.
Vyn, T.J. et al. Potassium fertilization effects on isoflavone concentrations in soybean [*Glycine max* (L.) *Merr.*], Journal of Agricultural and Food Chemistry, 2002, vol. 50, pp. 3501-3506.
Wargent, J.J. et al. Increased exposure to UV-B radiation during early development leads to enhanced photoprotection and improved long-term performance in *Lactuca sativa*, Plant, Cell & Environment, 2011, vol. 34, pp. 1401-1413.
Wu, M. et al. Computational Evidence for the Role of *Arabidopsis thaliana* UVR8 as UV-B Photoreceptor and Identification of Its Chromophore Amino Acids, Journal of Chemical Information and Modeling, 2011, vol. 51, pp. 1287-1295.
Zoratti et al. Light-controlled flavonoid biosynthesis in fruits. Frontiers In Plant Science 5(534):16 pgs (2014).
Aldemita et al., Agrobacterium tumefaciens-mediated transformation of japonica and indica rice varieties. Planta 199: 612-617 (1996).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1997).
An et al., Organ-Specific and Developmental Regulation of the Nopaline Synthase Promoter in Transgenic Tobacco Plants. Plant Physiol 88: 547-552 (1988).
Baerson et al., Developmental regulation of an acyl carrier protein gene promoter in vegetative and reproductive tissues. Plant Molecular Bio 22: 255-267 (1993).
Baerson et al., Identification of domains in an *Arabidopsis* acyl carrier protein gene promoter required for maximal organ-specific expression. Plant Mol Bio 1947-1959 (1994).
Baumann et al., The DNA Binding Site of the Dof Protein NtBBF1 is Essential for Tissue-Specific and Auxin-Regulated Expression of the rolB Oncogene in Plants. The Plant Cell 11: 323-333 (1999).
Bevan, Binary Agrobacterium vectors for plant transformation. Nucleic Acids Res 12(22): 8711-8721 (1984).
Bird et al., The tomato polygalacturonase gene and ripening-specific expression in transgenic plants. Plant Molecular Biology 11: 651-662 (1988).
Cho, et al. Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Christou et al., Production of Transgenic Rice (*Oryza sativa* L.) Plants from Agronomically Important Indica and Japonica Varieties via Electric Discharge Particle Acceleration of Exogenous DNA into Immature Zygotic Embryos. Bio/Technology 9: 957-962 (1991).
Cong et al. Multiplex genome engineering using CRISPR/Cas systems. Science 339(6121):819-23 (2013).
Dicarlo, et al. Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dong et al., Agrobacterium-mediated transformation of Javanica rice. Molecular Breeding 2: 267-276 (1996).
Fromm et al., An Octopine Synthase Enhancer Element Directs Tissue-Specific Expression and Binds ASF-1, a Factor from Tobacco Nuclear Extracts. The Plant Cell 1: 977-984 (1989).
Fromm et al., Inheritance and Expression of Chimeric Genes in the Progeny of Transgenic Maize Plants. Bio/Tech 8: 833-839 (1990).
Gordon-Kamm et al., Transformation of Maize Cells and Regeneration of Fertile Transgenic Plants. Plant Cell, 2.7 (Jul. 1990): 603-618.
Gudmundsson, et al. Genome-wide association and replication studies identify four variants associated with prostate cancer susceptibility. Nat Genet. Oct. 2009;41(10):1122-6. doi: 10.1038/ng.448. Epub Sep. 20, 2009.
Guevara-Garcia et al., A 42 bp fragment of the pmas 1' promoter containing an ocs-like element confers a developmental, wound and chemically inducible expression pattern. Plant Mol Bio 38: 743-753 (1998).
Henikoff et al. Amino acid substitution matrices from protein blocks. PNAS USA 89(22):10915-10919 (1992).
Herrera-Estrella, et al. Expression of chimaeric genes transferred into plant cells using a Ti-plasmid-denved vector. Nature. 1983; 303:209-213.
Hiei et al., Efficient transformation of rice (*Oryza sativa* L.) mediated by Agrobacterium and sequence analysis of the boundaries of the T-DNA. Plant J. 6(2): 271-282 (1994).

(56) References Cited

OTHER PUBLICATIONS

Hwang, et al. Efficient genome editing in zebrafish using a CRISPR-Cas system. Nat Biotechnol. Mar. 2013;31(3):227-9. doi: 10.1038/nbt.2501. Epub Jan. 29, 2013.
"Irradiance" Wikipedia (1999).
Ishida et al., High efficiency transformation of maize (*Zea mays* L.) mediated by Agrobacterium tumefaciens. Nat Biotechnol. 14(6): 745-750 (1996).
Jiang, et al. RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al.: Creating Heritable Mutations in *Drosophila* with CRISPR-Cas9; Science, 337:816-821 (2012).
"Kaempferol" Wikipedia (2011).
Kaiser et al., Cis-acting elements of the CHS1 gene from white mustard controlling promoter activity and spatial patterns of expression. Plant Mol Bio 28: 231-243 (1995).
Klee et al., Vectors for Transformation of Higher Plants. Bio/Technology 3: 637-642 (1985).
Makarova et al. Evolution and classification of the CRISPR-Cas systems. Nat Rev Microbiol 9:467-477 (2011).
Mali et al. RNA-guided human genome engineering via Cas9. Science 339(6121):823-826 (2013).
Odell et al., Identification of DNA sequences required for activity of the cauliflower mosaic virus 35S promoter. Nature 313(6005):810-812 (1985).
Ohl et al., Functional Properties of Phenylalanine Ammonia-Lyase Promoter from *Arabidopsis*. The Plant Cell 2: 837-848 (1990).
Out, et al. Deep sequencing to reveal new variants in pooled DNA samples. Hum Mutat. Dec. 2009; 30(12): 1703-12. doi: 10.1002/humu.21122.
PCT/IB19/01422 International Search Report and Written Opinion dated Jul. 24, 2020.
Ringli et al., Specific interaction of the tomato bZIP transcription factor VSF-1 with a non-palindromic DNA sequence that controls vascular gene expression. Plant Molecular Bio 37: 977-988 (1998).
Shi et al., Gibberellin and abscisic acid regulate GAST1 expression at the level of transcription. Plant Mol Bio 38: 1053-1060 (1998).
Shimamoto et al., Fertile transgenic rice plants regenerated from transformed protoplasts. Nature 338: 274-276 (1989).
Tohge et al., Transcriptional and metabolic programs following exposure of plants to UV-B irradiation. Plant Signaling & Behavior 6(12): 1987-1992 (2011).
Turner, et al. Massively parallel exon capture and library-free resequencing across 16 genomes. Nat Methods. May 2009; 6(5): 315-6. doi: 10.1038/nmeth.f.248. Epub Apr. 6, 2009.
Van der Kop et al., Selection of Arabidopsis mutants overexpressing genes driven by the promoter of an auxin-inducible glutathione S-transferase gene. Plant Mol Bio 39: 979-990 (1999).
Vasil et al., Herbicide Resistant Fertile Transgenic Wheat Plants Obtained by Microprojectile Bombardment of Regenerable Embryogenic Callus. Bio/Technology 10: 667-674 (1992).
Vasil et al., Regeneration of Plants from Embryogenic Suspension Culture Protoplasts of Wheat (*Triticum aestivum* L.) Bio/Technology 8: 429-434 (1990).
Voytas, Plant Genome Engineering with Sequence-Specific Nucleases. Annu. Rev. Plant Biol. 64: 327-350 (2013).
Wan et al., Generation of Large Nos. of Independently Transformed Fertile Barley Plants. Plant Physiol. 104(1): 37-48 (1994).
Weeks et al., Rapid Production of Multiple Independent Lines of Fertile Transgenic Wheat (*Triticum aestivum*). Plant Physiol. 102(4): 1077-1084 (1993).
Willmott et al., DNase1 footprints suggest the involvement of at least three types of transcription factors in the regulation of alpha-Amy2/A by gibberellin. Plant Mol Bio 38: 817-825 (1998).

Poulson et al., Enhanced tolerance of photosynthesis to high-light and drought stress in Pseudotsuga menziesii seedlings grown in ultraviolet-B radiation. Tree Physiology 22(12): 829-838 (2002).
U.S. Appl. No. 16/326,871 Non-Final Office Action dated Apr. 21, 2021.
Yang et al., Ultraviolet-B irradiation-induced freezing tolerance in relation to antioxidant system in winter wheat (*Triticum aestivum* L.) leaves. Environmental and Experimental Botany 60(3): 300-307 (2007).
Lai et al., Identifying metabolites by integrating metabolome databases with mass spectrometry cheminformatics. Nat Methods 15(1):53-56 (2018).
Tanaka et al., An ultraviolet-B-resistant mutant with enhanced DNA repair in *Arabidopsis*. Plant Physiol. 129(1):64-71 (2002).
Tsugawa et al., Hydrogen Rearrangement Rules: Computational MS/MS Fragmentation and Structure Elucidation Using MS-FINDER Software. Anal Chem. 88(16):7946-7958 (2016).
Extended European Search Report for EP Patent Application No. 22160092.7 dated Oct. 20, 2022.
Extended European Search Report issued in European Patent Application No. 19881025.1 on Jul. 20, 2022.
Falconí et al., Solar UV-B radiation limits seedborne anthracnose infection and induces physiological and biochemical responses in Lupinus mutabilis, Plant Pathology, vol. 68, No. 9, Dec. 8, 2019.
Musil, Accumulated effect of elevated ultraviolet-B radiation over multiple generations of the arid-environment annual *Dimorphotheca sinuata* DC. (Asteraceae). Plant, Cell and Environment 19: 1017-1027 (1996).
Shaukat SS, et al. Effect of enhanced UV-B radiation on germination, seedling growth and biochemical responses of *Vigna mungo* (L.) Hepper. Pak. J. Bot. May 1, 2013;45(3):779-85.
CN202310102904.4 Office Action dated May 8, 2024, and English translation.
Cohrs, et al. The Two Cryptochrome/Photolyase Family Proteins Fulfill Distinct Roles in DNA Photorepair and Regulation of Conidiation in the Gray Mold Fungus *Botrytis cinerea*. Appl Environ Microbiol. Aug. 17, 2017;83(17):e00812-17. doi: 10.1128/AEM.00812-17. Print Sep. 1, 2017.
Co-pending U.S. Appl. No. 18/784,549, inventor Wargent; Jason John, filed Jul. 25, 2024.
Kanto, Takeshi et al. UV-B Radiation for Control of Strawberry Powdery Mildew. Acta Horticulturae pp. 359-362, Aug. 2009.
Leclerc, Melen, et al., Estimating the Delay between Host Infection and Disease (Incubation Period) and Assessing Its Significance to the Epidemiology of Plant Diseases. PLOS One 9(1) e86568, 15 pages (2014).
McPartland, J.M. A review of Cannabis diseases. Journal of the International Hemp Association 3(1): 19-23. 1996. Available online at URL: http://www.internationalhempassociation.org/jiha/iha03111.html.
Suthaparan, et al. Suppression of Powdery Mildews by UV-B: Application Frequency and Timing, Dose, Reflectance, and Automation. Plant Dis. Aug. 2016;100(8):1643-1650. doi: 10.1094/PDIS-12-15-1440-RE. Epub Apr. 28, 2016.
The Prairie Ecologist, Essays, photos, and discussion about prairie ecology, restoration, and management, Lessons from the Grassland Restoration Network, posted Dec. 13, 2010 by Chris Helzer at https://prairieecologist.com/tag/broadcast-seeding/ Accessed on Apr. 29, 2024, 5 pages.
U.S. Appl. No. 17/315,012 Office Action dated Apr. 15, 2024.
U.S. Appl. No. 17/315,012 Office Action dated Aug. 26, 2022.
U.S. Appl. No. 17/315,012 Office Action dated Feb. 6, 2023.
U.S. Appl. No. 17/381,087 Office Action dated Apr. 10, 2024.
U.S. Appl. No. 17/381,087 Office Action dated Feb. 22, 2023.
U.S. Appl. No. 17/381,087 Office Action dated Sep. 7, 2023.
Yuan, Li et al. Ultraviolet Radiation Ecology. China Environmental Science Press. 1st Edition p. 9 (2000). (Chinese Language document).

* cited by examiner

METHOD TO IMPROVE CROP YIELD AND/OR QUALITY

CROSS-REFERENCE

This application is a continuation of International Patent Application No. PCT/IB2018/000839, filed on Jun. 29, 2018, which claims the benefit of U.S. Provisional Application No. 62/526,922 filed on Jun. 29, 2017, which is incorporated herein by reference in its entirety.

BACKGROUND

In the past, methods to improve crop yield and quality have typically relied on fertilizers, pesticides and other chemicals, or genetic breeding programs to select for beneficial traits. Alternatively, careful but costly manipulation or control of environmental factors such as temperature or irrigation during crop growth was relied upon in an effort to improve crop outcomes.

These approaches sometimes increase yield, but are not without disadvantages. Fertilizers and chemicals can lead to environmental pollution or health risks if improperly used. Proper use often involves considerable cost in money and time to apply to crops.

Genetic breeding has many advantages in terms of crop improvement, but is often a slow process and suffers from uncertain phenotypic outcomes. For instance, whilst one commercially important trait may be improved (such as disease resistance), it may come at a cost such as a deleterious effect on a separate trait such as taste or color.

Finally, careful control of growth conditions before harvest certainly is important. Yet less hardy plants often die due to stresses in the outdoor environment regardless of this control of growth conditions, and this leads to a net loss of production.

Historically, UV radiation has been seen as a detrimental treatment to plant seedlings, as it was believed to stress plants by subjecting them to photodamage and trigger inappropriate developmental responses. Yet, in more recent years, research has focused on treatment of certain plants with ultraviolet (UV) radiation and visible light to improve defense/protection mechanisms.

Behn et al. (Europ. J. Hort. Sci., 76(2). S. 33-40, 2011, ISSN 1611-4426) shows exposure of lettuce seedlings with filtered natural sunlight, containing UV-B, UV-A and visible light led to improved stress tolerance, but as a trade off led to a loss of biomass accumulation, thought to be due to a redirection of carbohydrate substrate from growth to secondary metabolism (i.e. protection mechanisms). Whilst the plants showed improved defense/protection, crop yield and quality diminished.

WO 2012/085336 describes a device to deliver a combination of UV-A (315-400 nm), UV-B (280-315), violet and blue (400-500 nm) and red and far red (600-800 nm) light, optionally also with green and yellow light (500-600 nm). The device was used to treat tree seedlings and it was suggested this prevented transplantation shock while the plants are moved from an indoor setting to an outdoor setting for plant growth. Specifically, it discloses that the device's treatment shortened the growth cycle of tree seedlings, enhances the proportion of viable seedlings and eliminates one work phase in the growth process (e.g. removing the need for sunshade curtains), thus improving the economics of seedling cultivation. Yet, WO 2012/085336 is only focused on seedling viability and the economics of seedling cultivation, not towards improving crop yield and/or quality. Additionally, it relies on multiple UV wavebands, which may complicate the treatment process and/or may lead to undesirable traits, such as those described in Behn et al.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

The disclosure is summarized in part by the claims as attached hereto. It is understood that the disclosure further encompasses material not explicitly recited in the claims attached hereto, and that alternate claim language is consistent with and supported by the disclosure herein.

Provided herein are methods of treating a plant seedling to improve long term hardiness and/or improve crop yield and/or quality characterized by the step of exposing the plant seedling, prior to a subsequent growth phase, with ultraviolet (UV) irradiation with at least one wavelength, only between 280-310 nm. Further provided herein are methods, wherein the treatment of the plant seedling with UV irradiation is performed indoors. Further provided herein are methods further comprising exposing the plant seedling to UV light in the range of 2-15 days. Further provided herein are methods further comprising exposing the plant seedling to cyclic exposure of UV light. Further provided herein are methods further comprising maintaining the temperature at approximately between 12° C. to 35° C. during the treatment. Further provided herein are methods further comprising exposure to UV wavelength within the range 280-305 nm. Further provided herein are methods further comprising exposure to peak UV wavelength within the range 280-290 nm. Further provided herein are methods, wherein the plant seedling is a fruit and vegetable species. Further provided herein are methods, wherein the plant seedling is selected from the group including green lettuce, red lettuce, tomato, cucumber, broccoli, herb crops and eggplant.

Provided herein are devices to administer ultraviolet (UV) irradiation to a plant seedling, characterized in that the device is configured to administer ultraviolet (UV) irradiation with at least one wavelength within the range 280-310 nm. Further provided herein are devices, wherein the device includes a moving conveyor which alters the relative positions of at least one light emitter and the target area during the treatment. Further provided herein are devices, wherein the light emitter is at least one light emitting diode (LED). Further provided herein are devices, wherein the device is configured to also administer at least one wavelength in the visible spectrum between 400 to 800 nm. Further provided herein are devices, wherein the device is configured to administer at least one a wavelength in the blue visible spectrum between 400 to 500 nm. Further provided herein are devices, wherein the device is configured to administer at least one a wavelength in the red visible spectrum between 655-680 nm.

Provided herein are methods of improving long term hardiness and/or crop yield and/or crop quality characterized by the steps of (a) exposing a plant seedling or seedlings, prior to a subsequent growth phase, with ultraviolet (UV) light with at least one wavelength, only within the range 280-310 nm; and (b) selecting a plant seedling or seedlings for a subsequent growth phase. Further provided herein are methods, wherein step (b) includes predicting or assessing hardiness of the plant seedling and/or resulting crop yield or crop quality of the plant seedling(s) or plant in order to select for seedling(s) or related seedling(s) undergoing similar UV treatment which show promising beneficial traits.

Provided herein are plant seedlings, plant or harvestable crop following treatment according to any methods described herein.

Provided herein are methods for improving hardiness and plant yield, comprising administering light enriched for UV wavelengths from 280 nm to 290 nm to a plant material. Further provided herein are methods, wherein the plant material comprises material of a plant in family Rosaceae. Further provided herein are methods, wherein the Rosaceae material is of a plant in genus a *Fragaria*. Further provided herein are methods, wherein the plant material is a runner. Further provided herein are methods, wherein the plant material is a seed. Further provided herein are methods, wherein the plant material is a seedling. Further provided herein are methods, wherein the plant material is a plant. Further provided herein are methods, wherein the light is enriched for a UV wavelength of 280 nm. Further provided herein are methods, wherein the light is enriched for a UV wavelength of 290 nm. Further provided herein are methods wherein the light comprises blue light. Further provided herein are methods, wherein the light comprises red light. Further provided herein are methods, wherein the light is administered for at least 1 day. Further provided herein are methods, wherein the light is administered for at least 14 days. Further provided herein are methods, wherein the light is administered for about 14 days. Further provided herein are methods, wherein the yield is selected from a group consisting of an improved fruit fresh weight, improved number of fruit harvested, improved Brix content, improved fruit width, improved fruit length, improved leaf size, an improved leaf surface area, an improved dry weight, an improved nitrogen content, an improved shoot dry weight, an improved shoot fresh weight, an improved root dry weight, an improved vegetable development, an improved yield of fruiting parts, an increased weight of fruiting parts, improved hardiness, and an increased seed germination rate. Further provided herein are methods, wherein the yield is improved by at least 5% compared to a plant from a non-UV-B irradiated seed. Further provided herein are methods, wherein the hardiness is selected from a group consisting of an improved resistance to stress caused by weather damage, an improved resistance to stress caused by sun exposure, an improved resistance to stress caused by disease, and an improved resistance to stress caused by insects.

Provided herein are methods of growing a crop by reducing pesticide use without impacting loss due to pest damage comprising the steps of: (a) administering light enriched for at least one UV wavelength in a range from 280 nm to 290 nm to a plant material; (b) providing no more than 95% of the standard pesticide regimen; and (c) harvesting the crop, wherein the crop provides a greater yield than a comparable crop provided with the standard pesticide regimen but not supplemented with UV light.

Provided herein are methods for improving hardiness and plant yield in a crop, comprising (a) administering light enriched for at least one UV wavelength in a range from 280 nm to 290 nm to a plant material; (b) providing a pesticide regimen, wherein the pesticide regimen is no more than 50% of the standard pesticide regimen; (c) harvesting the crop, and (d) measuring the plant yield, wherein the crop provides a greater yield than a comparable crop provided with the standard pesticide regimen but not supplemented with UV light. Further provided herein are methods, wherein the plant material comprises plant material from a plant in family Rosaceae. Further provided herein are methods, wherein the Rosaceae plant is of genus *Fragaria*. Further provided herein are methods, wherein the plant material is a runner. Further provided herein are methods, wherein the plant material is a seed. Further provided herein are methods, wherein the plant material is a seedling. Further provided herein are methods, wherein the plant material is a plant. Further provided herein are methods, wherein the light is enriched for UV wavelength of 280 nm. Further provided herein are methods, wherein the light is enriched for UV wavelength of 290 nm. Further provided herein are methods, wherein the light comprises blue light. Further provided herein are methods, wherein the light comprises red light. Further provided herein are methods, wherein the light is administered for at least 1 day. Further provided herein are methods, wherein the light is administered for at least 14 days. Further provided herein are methods, wherein the light is administered for about 14 days. Further provided herein are methods, wherein the yield is selected from a group consisting of an improved fruit fresh weight, improved number of fruit harvested, improved Brix content, improved fruit width, improved fruit length, improved leaf size, an improved leaf surface area, an improved dry weight, an improved nitrogen content, an improved shoot dry weight, an improved shoot fresh weight, an improved root dry weight, an improved vegetable development, an improved yield of fruiting parts, an increased weight of fruiting parts, improved hardiness, and an increased seed germination rate. Further provided herein are methods, wherein the yield is improved by at least 5% compared to a plant from a non-UV-B irradiated seed. Further provided herein are methods, wherein the hardiness is selected from a group consisting of an improved resistance to stress caused by weather damage, an improved resistance to stress caused by sun exposure, an improved resistance to stress caused by disease, and an improved resistance to stress caused by insects. Further provided herein are methods, wherein the pesticide regimen is no more than 60% of the standard pesticide regimen. Further provided herein are methods, wherein the pesticide regimen is no more than 70% of the standard pesticide regimen. Further provided herein are methods, wherein the pesticide regimen is no more than 80% of the standard pesticide regimen.

Provided herein are crops resulting from any of the methods described herein.

Provided herein are fields subjected to treatment comprising any of the methods described herein.

Provided herein are methods for improving yield of a fruiting component of a crop plant, comprising: administering light enriched for at least one UV wavelength in a range from 280 nm to 290 nm to a plant material at least 7 weeks before fruit is harvested. Further provided herein are methods, wherein the light is enriched for UV wavelength of 280 nm. Further provided herein are methods, wherein the light is enriched for UV wavelength of 290 nm. Further provided herein are methods, wherein the light comprises blue light. Further provided herein are methods, wherein the light comprises red light. Further provided herein are methods, wherein the light is administered using a treatment regimen for a duration of at least 1 day. Further provided herein are methods, wherein the light is administered using a treatment regimen for a duration of at least 14 days. Further provided herein are methods, wherein the light is administered using a treatment regimen for a duration of about 14 days. Further provided herein are methods, wherein the light is administered for about 10 hours total per day. Further provided herein are methods, wherein the plant material is from a plant in family Rosaceae. Further provided herein are methods, wherein the Rosaceae plant is of genus *Fragaria*. Further provided herein are methods, wherein the plant material is from a fruiting plant. Further provided herein are methods, wherein the plant material is from at least one of tomato, strawberry, and *cannabis*. Further provided herein are methods, wherein the plant material is a runner. Further provided herein are methods, wherein the plant material is a seed. Further provided herein are methods, wherein the plant material is a seedling. Further provided herein are methods, wherein the plant material is a plant. Further provided herein are methods, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Further provided herein are methods, wherein the improved yield is fruit fresh weight. Further provided herein are methods, wherein the fruit fresh weight is improved by at least 5% compared to a non-UV-B irradiated plant material. Further provided herein are methods, wherein the improved yield is number of fruit harvested. Further provided herein are methods, wherein the number of fruit harvested is improved by at least 10% compared to a non-UV-B irradiated plant material. Further provided herein are methods, wherein the improved yield is increased flowering parts. Further provided herein are methods, wherein the improved yield is improved Brix content. Further provided herein are methods, wherein the yield is improved by at least 5% compared to a non-UV-B irradiated plant material.

Provided herein are methods for improving yield of a fruiting component of a crop plant, comprising: administering light enriched for at least one UV wavelength, such as a wavelength in a range of 280-320 nm, or in a narrower range of 280 nm to 300 nm, 280 nm to 295 nm, or 280 nm to 290 nm to a plant material during a propagation stage of the plant material. Further provided herein are methods, wherein the light is enriched for UV light at a wavelength of at least one of 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 nm. In some such methods the light is enriched for UV at a wavelength of 290 nm. In some such methods the light is enriched for UV at a wavelength of 280 nm. Further provided herein are methods, wherein the light comprises blue light. Further provided herein are methods, wherein the light comprises red light. Further provided herein are methods, wherein the light is administered using a treatment regimen for a duration of at least 1 day, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more than 30 days. Further provided herein are methods, wherein the light is administered using a treatment regimen for a duration of at least 14 days. Further provided herein are methods, wherein the light is administered using a treatment regimen for a duration of about 14 days. Further provided herein are methods, wherein the light is administered using a treatment regimen for a duration of no more than 14 days. Further provided herein are methods, wherein the light is administered for about 10 hours total per day. Further provided herein are methods, wherein the plant material is from a plant in family Rosaceae, such as a Rosaceae plant of the genus *Fragaria*. Further provided herein are methods, wherein the plant material is from a fruiting plant. Further provided herein are methods, wherein the plant material is from at least one of tomato, strawberry, and *cannabis*. Further provided herein are methods, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Further provided herein are methods, wherein the improved yield is fruit fresh weight. Further provided herein are methods, wherein the fruit fresh weight is improved by at least 5% compared to a non-UV-B irradiated plant material. Further provided herein are methods, wherein the improved yield is number of fruit harvested. Further provided herein are methods, wherein the number of fruit harvested is improved by at least 10% compared to a non-UV-B irradiated plant material. Further provided herein are methods, wherein the improved yield is increased flowering parts. Further provided herein are methods, wherein the improved yield is improved Brix content. Further provided herein are methods, wherein the improved yield is improved by at least 5% compared to a non-UV-B irradiated plant material. Further provided herein are methods, wherein the improved yield occurs at least 1 week following administration of the light. Further provided herein are methods, wherein the improved yield occurs 1 week, 2 weeks, 3 weeks, 4 weeks, 5 weeks, 6 weeks, 7 weeks, or 8 weeks following administration of the light. Further provided herein are methods, wherein the propagation stage comprises runners. Further provided herein are methods, wherein the propagation stage comprises shoots. Further provided herein are methods, wherein the propagation stage comprises cuttings.

Provided herein are methods for improving yield of a fruiting component of a crop plant, comprising: (a) administering light enriched for at least one UV wavelength, such as UV in a wavelength range from 280 nm to 300 nm, 290 nm to 300 nm, or in a range from 280 nm to 290 nm to a plant material; and (b) collecting an increased number of fruit than expected number of fruit for an untreated field. Further provided herein are methods, wherein the light is enriched for UV light at a wavelength of at least one of 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 nm, such as a wavelength of 280 nm or 290 nm. Further provided herein are methods, wherein the light comprises blue light. Further provided herein are methods, wherein the light comprises red light. Further provided herein are methods, wherein the light is administered using a treatment regimen for a duration of at least 1 day, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more than 30 days. Further provided herein are methods, wherein the light is administered using a treatment regimen for a duration of at least 14 days. Further provided herein are methods, wherein the light is administered using a treatment regimen for a duration of about 14 days. Further provided herein are methods, wherein the light is administered using a treatment regimen for a duration of no more than 14 days. Further provided herein are methods, wherein the light is administered for about 10 hours total per day. Further provided herein are methods, wherein the plant material is from a crop plant, such as a row crop or a fruiting crop. In some cases the plant is of the plant in family Poaceae, Asteraceae, Fabaceae, Brassicaceae, Lamiaceae, Solanaceae, Cannabaceae, or Rosaceae. Further provided herein are methods, wherein the plant is of genus *Solanum, Lycopersicon, Cannabis*, or *Fragaria*. Further provided herein are methods, wherein the plant material is from a fruiting plant. Further provided herein are methods, wherein the plant material is from at least one of tomato, strawberry, and *cannabis*. Further provided herein are methods, wherein the number of fruit is increased by at least 5%. Further provided herein are methods, wherein the increase is measured relative to a reference, such as and expected number of fruit determined by a national average, a historical average for a growing region, or an untreated field, among others. Further provided herein are methods, wherein the untreated field comprises an adjacent field. Further provided herein are methods, wherein the untreated field comprises a field of about the same size, same latitude, same climate zone, same sunlight exposure, same daytime temperature, same night time temperature, same water exposure, or other parameters facilitating a comparison.

Provided herein are methods for improving yield of a fruiting component of a crop plant, comprising: administering light enriched for at least one UV wavelength, such as a UV wavelength in a range from 280 nm to 290 nm, 290 nm to 300 nm, or 300 nm to 320 nm to a plant material, wherein the yield is improved by at least 5%. Further provided herein are methods, wherein the light is enriched for UV light at a wavelength of at least one of 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 nm, such as a wavelength of 280 nm or 290 nm. Further provided herein are methods, wherein the light comprises blue light. Further provided herein are methods, wherein the light comprises red light. Further provided herein are methods, wherein the light is administered using a treatment regimen for a duration of at least 1 day. Further provided herein are methods, wherein the light is administered using a treatment regimen for a duration of at least 14 days. Further provided herein are methods, wherein the light is administered using a treatment regimen for a duration of about 14 days. Further provided herein are methods, wherein the light is administered for about 10 hours total per day. Further provided herein are methods, wherein the plant material is from a plant in family Rosaceae. Further provided herein are methods, wherein the Rosaceae plant is of genus *Fragaria*. Further provided herein are methods, wherein the plant material is from a fruiting plant. Further provided herein are methods, wherein the plant material is from at least one of tomato, strawberry, and *cannabis*. Further provided herein are methods, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Further provided herein are methods, wherein the improved yield is fruit fresh weight. Further provided herein are methods, wherein the improved yield is number of fruit harvested. Further provided herein are methods, wherein the improved yield is increased flowering parts. Further provided herein are methods, wherein the improved yield is improved Brix content. Further provided herein are methods, wherein the improved yield is compared to a non-UV-B irradiated plant material.

Provided herein are fields having at least 10% improved yield of fruiting components of a crop plant following administration of light enriched for UV-B in a range of 280 nm to 290 nm compared to a field not administered UV-B. Provided herein are fields having more than about 50000 pounds of fruiting components of a crop plant per acre following administration of light enriched for UV-B in a range of 280 nm to 290 nm compared to a field not administered UV-B. Further provided herein are fields, wherein no more than 95% of at least one of a standard fertilizer regimen, standard pesticide regimen, standard herbicide regimen, standard insecticide regimen, and standard water regimen is administered. Further provided herein are fields, wherein no more than 80% of at least one of a standard fertilizer regimen, standard pesticide regimen, standard herbicide regimen, standard insecticide regimen, and standard water regimen is administered. Further provided herein are fields, wherein no more than 70% of at least one of a standard fertilizer regimen, standard pesticide regimen, standard herbicide regimen, standard insecticide regimen, and standard water regimen is administered. Further provided herein are fields, wherein no more than 60% of at least one of a standard fertilizer regimen, standard pesticide regimen, standard herbicide regimen, standard insecticide regimen, and standard water regimen is administered. Further provided herein are fields, wherein the light is enriched for UV wavelength of 280 nm. Further provided herein are fields, wherein the light is enriched for UV wavelength of 290 nm. Further provided herein are fields, wherein the light comprises blue light. Further provided herein are fields, wherein the light comprises red light. Further provided herein are fields, wherein the light is administered using a treatment regimen for a duration of at least 1 day. Further provided herein are fields, wherein the light is administered using a treatment regimen for a duration of at least 14 days. Further provided herein are fields, wherein the light is administered using a treatment regimen for a duration of about 14 days. Further provided herein are fields, wherein the light is administered for about 10 hours total per day. Further provided herein are fields, wherein the crop plant is from a plant in family Rosaceae. Further provided herein are fields, wherein the Rosaceae plant is of genus *Fragaria*. Further provided herein are fields, wherein the crop plant is from at least one of tomato, strawberry, and *cannabis*. Further provided herein are fields, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Further provided herein are fields, wherein the improved yield is fruit fresh weight. Further provided herein are fields, wherein the improved yield is number of fruit harvested. Further provided herein are fields, wherein the improved yield is increased flowering parts. Further provided herein are fields, wherein the improved yield is improved Brix content.

Provided herein are methods for improving yield of a fruiting component of a crop plant, comprising: subjecting a plant material to a treatment regimen comprising light enriched for at least one UV wavelength in a range from 280 nm to 295 nm and at least one of a treatment distance from the plant material and a light source in a range of about 30 mm to about 120 mm, a speed of a moving light source in a range of about 40 to about 60 mm per second, a light source timing cycle in a range of about 90 to about 280 seconds, a number of cycles per day in a range of about 380 to about 500 cycles per day, an irradiance of the UV wavelength in a range of about 15 to about 40 umol cm$^{-2}$ s$^{-1}$, a wavelength of blue light in a range of about 440 nm to about 460 nm, an irradiance of blue light in a range of about 30 to about 150 umol m$^{-2}$ s$^{-1}$, a wavelength of red light in a range of about 640 nm to about 680 nm, an irradiance of red light in a range of about 60 to about 300 umol m$^{-2}$ s$^{-1}$, and a number of days of the treatment regimen in a range of about 5 to about 20 days. Further provided herein are methods, wherein the at least one UV wavelength is peaking at 282 nm. Further provided herein are methods, wherein the at least one UV wavelength is peaking at 285 nm. Further provided herein are methods, wherein the at least one UV wavelength is peaking at 287 nm. Further provided herein are methods, wherein the at least one UV wavelength is peaking at 291 nm. Further provided herein are methods, wherein the at least one UV wavelength is peaking at 292 nm. Further provided herein are methods, wherein the plant material is from at least one of tomato, strawberry, and *cannabis*. Further provided herein are methods, wherein the plant material is a runner. Further provided herein are methods, wherein the plant material is a seed. Further provided herein are methods, wherein the plant material is a seedling. Further provided herein are methods, wherein the plant material is a plant. Further provided herein are methods, wherein the crop plant is from a plant in family Rosaceae. Further provided herein are methods, wherein the Rosaceae plant is of genus *Fragaria*. Further provided herein are methods, wherein the crop plant is from at least one of tomato, strawberry, and *cannabis*. Further provided herein are methods, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Further provided herein are methods, wherein the improved yield is fruit fresh weight. Further provided herein are methods, wherein the improved yield is number of fruit harvested. Further provided herein are methods, wherein the improved yield is increased flowering parts. Further provided herein are methods, wherein the improved yield is improved Brix content. Further provided herein are methods, wherein the improved yield is improved by at least 5%.

Provided herein are devices configured to administer a treatment regimen comprising light enriched for at least one UV wavelength in a range from 280 nm to 295 nm to a plant material and to control at least one of a treatment distance from the plant material and a light source in a range of about 30 mm to about 120 mm, a speed of a moving light source in a range of about 40 to about 60 mm per second, a light source timing cycle in a range of about 90 to about 280 seconds, a number of cycles per day in a range of about 380 to about 500 cycles per day, an irradiance of the UV wavelength in a range of about 15 to about 40 umol cm$^{-2}$ s$^{-1}$, a wavelength of blue light in a range of about 440 nm to about 460 nm, an irradiance of blue light in a range of about 30 to about 150 umol m$^{-2}$ s$^{-1}$, a wavelength of red light in a range of about 640 nm to about 680 nm, an irradiance of red light in a range of about 60 to about 300 umol s$^{-1}$, and a number of days of the treatment regimen in a range of about 5 to about 20 days. Further provided herein are devices, wherein the at least one UV wavelength is peaking at 282 nm. Further provided herein are devices, wherein the at least one UV wavelength is peaking at 285 nm. Further provided herein are devices, wherein the at least one UV wavelength is peaking at 287 nm. Further provided herein are devices, wherein the at least one UV wavelength is peaking at 291 nm. Further provided herein are devices, wherein the at least one UV wavelength is peaking at 292 nm. Further provided herein are devices, wherein the plant material is from at least one of tomato, strawberry, and *cannabis*. Further provided herein are devices, wherein the plant material is a runner. Further provided herein are devices, wherein the plant material is a seed. Further provided herein are devices, wherein the plant material is a seedling. Further provided herein are devices, wherein the plant material is a plant. Further provided herein are devices, wherein the crop plant is from a plant in family Rosaceae. Further provided herein are devices, wherein the Rosaceae plant is of genus *Fragaria*. Further provided herein are devices, wherein the crop plant is from at least one of tomato, strawberry, and *cannabis*. Further provided herein are devices, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Further provided herein are devices, wherein the improved yield is fruit fresh weight. Further provided herein are devices, wherein the improved yield is number of fruit harvested. Further provided herein are devices, wherein the improved yield is increased flowering parts. Further provided herein are devices, wherein the improved yield is improved Brix content. Further provided herein are devices, wherein the improved yield is improved by at least 5%.

BRIEF DESCRIPTION OF DRAWINGS

Further aspects of the present disclosure will become apparent from the following description which is given by way of example only and with reference to the accompanying drawings in which.

Figure 1:
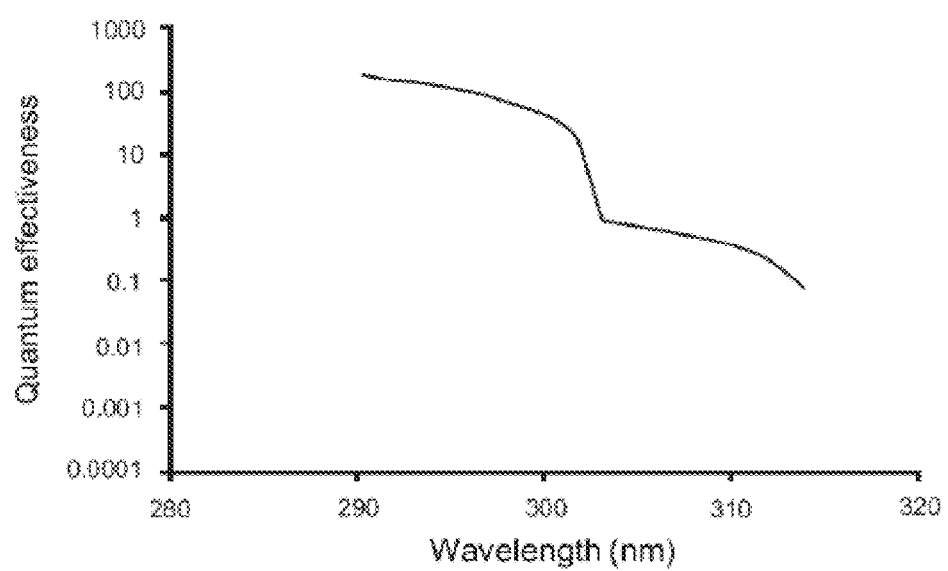
FIG. 1 depicts an analysis of UV spectrum to provide beneficial hardiness outcome.

Further aspects of the present disclosure will become apparent from the following description which is given by way of example only and with reference to the accompanying drawings.

DETAILED DESCRIPTION

Disclosed herein are methods, devices and recipes for treating a plant seedling or other plant material to improve long term hardiness and/or improve crop yield and/or crop quality characterized by the step of exposing the plant seedling, prior to a subsequent growth phase, with ultraviolet (UV) irradiation with at least one wavelength only between 280-310 nm.

According to another aspect of the present disclosure there is provided a device to administer ultraviolet (UV) irradiation to a plant seedling or plant material, characterized in that the device is configured to administer ultraviolet (UV) irradiation with at least one wavelength in a range of about 280 to about 320 nm, such as UV light having a peak wavelength at a wavelength of at least one of 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 nm, such as a wavelength of 280 nm or 290 nm or in a range of 280 nm to 310 nm. The treatment may further comprise a treatment distance from the plant material and a light source in a range of about 30 mm to about 120 mm, a speed of a moving light source in a range of about 40 to about 60 mm per second, a light source timing cycle in a range of about 90 to about 280 seconds, a number of cycles per day in a range of about 380 to about 500 cycles per day, an irradiance of the UV wavelength in a range of about 15 to about 40 umol cm$^{-2}$ s$^{-1}$, a wavelength of blue light in a range of about 440 nm to about 460 nm, an irradiance of blue light in a range of about 30 to about 150 umol m$^{-2}$ s$^{-1}$, a wavelength of red light in a range of about 640 nm to about 680 nm, or an irradiance of red light in a range of about 60 to about 300 umol m$^{-2}$ s$^{-1}$.

According to another aspect of the present disclosure there is provided a method of improving long term hardiness and/or crop yield and/or crop quality including the step of
(a) exposing a plant seedling or plant material prior to a subsequent growth phase, with ultraviolet (UV) light with at least one wavelength only between 280-310 nm further characterized by the step of
(b) selecting, or determining an appropriate level of hardiness in, a plant seedling or plant material for the subsequent growth phase.

According to another aspect of the present disclosure there is provided a plant seedling, plant or harvestable crop which has been treated using the methods described herein.

Provided herein are methods of treating the plant seedling or plant material to increase crop yield and/or quality. In some instances, a direct correlation is observed between treatment of plant seedling or plant material with specific wavelengths in the UV-B spectrum and commercially important crop yield and quality. In some instances, methods as described herein comprise administration of light enriched or supplemented with UV-B. In some instances, part of this set of wavelengths is not found in the sunlight reaching the earth's surface, and is therefore differentiated from any form of treatment using natural sunlight.

Furthermore, the treatment also still appears to achieve desirable or improved hardiness (i.e. protection) from stresses such as abiotic and biotic stresses. For instance, in preliminary trials, cucumbers were shown to have an increased resistance/protection to cold stress (abiotic stress reduction) in older plants at final harvest 12 days after initial UV treatment of cucumber seedlings.

As another example, green lettuce was shown to have an increased resistance to fungal disease (biotic stress reduction) even in older plants. This illustrates the follow-on protective effects of the UV-treatment in older plants. Importantly, in both examples, crop yields were also increased at harvest. Therefore, the present disclosure is providing increased hardiness, and unlike Behn et al., also improved crop yield and quality. Behn et al taught away from the results of the present disclosure because it directed the reader to UV treatment causing the plants to build protection mechanisms at the loss of increased crop yield.

Additionally, unlike Behn et al., the treatment of the present disclosure may only require UV irradiation in one defined spectrum (and specifically only a subset of that), whereas Behn et al. had uncontrolled treatment in UV-A, UV-B and visible light, via filtered natural sunlight.

Unlike prior art broad spectrum UV treatment methods for improving stress resistance (e.g. to avoid transplantation shock), the present disclosure may use treatments within only one UV spectrum (within UV-B) which may substantially ease the treatment process and equipment needed.

Additionally, many treatments utilize sunlight as a UV-B, UV-A, and visible source, and result in a lack of specificity of dosage, often leading to undesirable and/or unpredictable results. The present disclosure often avoids this unpredictability due to only using specific wavelengths in a single defined waveband in the treatment. In some instances, plant seedlings are exposed to other background light during the treatment.

In some instances, use of a wavelength or wavelengths in a specific and narrow focused range within UV-B radiation between 280-310 nm leads to beneficial results. In some instances, part of the UV-B spectrum above about 310 nm does not lead to the beneficial results seen. As will be discussed further, the UV-B spectrum covers 280 nm to about 315 nm (however, defined separations between UV wavebands are approximate, and are subject to at least two common variations in the literature, i.e. including an upper limit for UV-B of 320 nm (IARC monographs on the evaluation of carcinogenic risks to humans. Volume 55—Solar and ultraviolet radiation; Chapter 1; Exposure data (1992)). It is possible that broader treatment within the UV-B spectrum or uncontrolled UV treatment may lead to deleterious results.

The long term hardiness of the plant refers to improved resistance to stresses encountered such as weather damage, sun exposure, disease and/or insect pest attack during the growth phase of the plant prior to harvest. Without wishing to be bound by theory, the commercial end result of an improved yield and/or quality of the crop at harvest is thought be at least partially attributed to an improved long-term hardiness resulting from the treatment. Regardless, the end result of improved crop yield and/or quality is observed as a result of this treatment method.

In some instances, using UV radiation outside of the UV-B range (for example the UV-A or UV-C wavelengths) does not lead to beneficial results. In some instances, beneficial effects dramatically diminish or disappear entirely when moving out of the UV-B spectrum, for instance into the UV-A spectrum (400 to 315 nm).

Described herein are methods for improving quality of the crop including at least one of improved taste, size, shape, colour, texture, visual appearance, shelf life and/or ability to withstand post-harvest handling. In some instances, methods comprise tracking, selecting for, or predicting for plants that will display improved hardiness and/or crop yield/quality following the described UV treatment. In some instances, this is beneficial to reduce attrition of plants prior to harvest, and therefore improve crop quality and/or yield.

Throughout the specification the phrase "prior to a subsequent growth phase" should be taken as meaning either prior to the plant seedling being transferred into an outdoor environment, or in some cases being retained indoors, at a particular time point based on the age, size other feature of the plant seedling or environmental characteristics. The growth phase of the plant is typically the phase when the plant exhibits substantial growth and development into a mature plant prior to harvesting.

Throughout this specification the term "hardiness" should be taken as meaning the ability of a plant to withstand or help protect against one or more stresses during crop production and which may allow for more desirable yield and/or quality of the plant at harvesting.

Throughout this specification the term "plant seedling" should be taken as meaning a young plant following germination from a seed. The plant seedling may be of a vegetable, fruit, tree, shrub, herb, grass origin, and so forth.

Throughout this specification the term "plant" should be taken as meaning a matured plant seedling which is ultimately used for crops or other applications.

Although the present disclosure has particular application to vegetable and fruit crop production, it is also possible the disclosure may be used to improve other types of plant hardiness such as trees, grasses, flowers, herbs and so forth. For simplicity, the remainder of the specification will refer to crop production (and particularly vegetables), although it should be appreciated this is not intended to be limiting.

Throughout this specification the term "crop" should be taken as meaning a cultivated plant which is harvested typically by a human or machine at some point during its growth stage for further use or human consumption. However, it should be appreciated that application of the methods to grasses, trees and so forth, may be used merely to improve the hardiness without any intention to harvest.

Throughout this specification the term "indoors" should be taken as meaning a housing, typically a greenhouse, plastic polytunnel, a shade cloth with no walls, or fully indoor system which might use artificial lighting.

In the example of a greenhouse, it may include transparent walls and/or ceiling to allow natural light in. The indoor housing may be used to allow the initial germination and seedling development phase to occur and is used during the UV irradiation exposure of the present disclosure prior to a subsequent growth phase in an outdoor environment.

In some embodiments, the treatment of the plant seedlings or plant material occurs indoors. For example, any one of the methods may occur indoors, for example, a greenhouse. In some instances, UV-B is administered indoors. In some instances, UV-B is administered outdoors. In some instances, UV-B is administered outdoors in a field.

In some instances, an advantage of conducting the treatment indoors is that it may help to regulate the conditions whilst the plant seedling is particularly vulnerable. Additionally, it may mean that the device used to apply the UV treatment may be better protected and secured. However, it is possible the treatment of the present disclosure may also be conducted in an outdoor environment, depending on the circumstances and type of seedlings or plant material to be treated.

Throughout this specification the term "transplantation" should be taken as meaning the act of transferring the plant seedling into an outdoor environment such as a field to allow continued growth prior to ultimate harvesting of the crops. The term transplantation shock refers specifically to the stress or shock incurred by the plant at the time of transplantation, for instance due to sun shock due to the different sun exposure seen between indoors and the outdoor environment.

Throughout this specification the term "ultraviolet (UV) irradiation" should be taken as meaning electromagnetic radiation with a wavelength shorter than visible light, but longer than X-rays, and is in between the range of 10 nm to 400 nm (corresponding to 3 eV to 124 eV). The ultraviolet (UV) irradiation spectrum is considered to be invisible to humans, and therefore differentiated from visible light in the spectrum of about 400 nm to 700 nm.

The ultraviolet spectrum can be further broken down into UV-A (400-320 nm), UV-B (320-280 nm) and UV-C (280-100 nm).

Methods as described herein, in some embodiments, comprise exposure to UV wavelength of about 280 to about 305 nm. In some instances, the beneficial effects are most pronounced within a narrower band of the UV-B spectrum, particularly between 280-305 nm.

In some instances, beneficial results are still seen beyond 305 nm, but the beneficial results drop sharply after moving beyond a wavelength of about 310 nm. For example, a UV light treatment peaking at 319 nm is still within the UV-B waveband of the spectrum, yet do not appear to produce desired effects. The present disclosure, in some instances, uses wavelengths in the short-wave range of the UV-B spectrum, a proportion of which exist outside of the natural spectrum of sunlight that reach the earth's surface. In some instances, UV treatment in the UV-A spectrum (at 354 nm) or treatment in the UV-C spectrum (at 270 nm) is not effective to improve hardiness.

In some instances, the method includes exposure to a peak UV wavelength of about 280 to about 290 nm. In some instances, treatment with UV light peaking between 280-290 nm showed promising results. In some instances, the method includes only a specific wavelength (or at least a wavelength peak) between 280-310 nm. In some instances, methods as described herein comprise a small amount of UV light that extends partially outside of the 280-310 nm range. In some instances, methods comprise insignificant background irradiation. This effect would be minor and would be appreciated by someone skilled in the art to have no real influence on the disclosure's benefits.

Methods as described herein comprise administration of UV-B in a range of about 280 nm to about 320 nm. In some cases, UV-B is administered at 280 nm (±5 nm), 286 nm (±5 nm), 294 nm (±5 nm), or about 317 nm. The UV-B can be about 280 nm, about 281 nm, about 282 nm, about 283 nm, about 284 nm, about 285 nm, about 286 nm, about 287 nm, about 288 nm, about 289 nm, about 290 nm, about 291 nm, about 292 nm, about 293 nm, about 294 nm, about 295 nm, about 296 nm, about 297 nm, about 298 nm, about 299 nm, about 300 nm, about 301 nm, about 302 nm, about 303 nm, about 304 nm, about 305 nm, about 306 nm, about 307 nm, about 308 nm, about 309 nm, about 310 nm, about 311 nm, about 312 nm, about 313 nm, about 314 nm, about 315 nm, about 316 nm, about 317 nm, about 318 nm, about 319 nm, or about 320 nm. In some cases, UV-B is peaking at 280 nm (±5 nm), 286 nm (±5 nm), 294 nm (±5 nm), or about 317 nm. The UV-B can be about 280 nm, about 281 nm, about 282 nm, about 283 nm, about 284 nm, about 285 nm, about 286 nm, about 287 nm, about 288 nm, about 289 nm, about 290 nm, about 291 nm, about 292 nm, about 293 nm, about 294 nm, about 295 nm, about 296 nm, about 297 nm, about 298 nm, about 299 nm, about 300 nm, about 301 nm, about 302 nm, about 303 nm, about 304 nm, about 305 nm, about 306 nm, about 307 nm, about 308 nm, about 309 nm, about 310 nm, about 311 nm, about 312 nm, about 313 nm, about 314 nm, about 315 nm, about 316 nm, about 317 nm, about 318 nm, about 319 nm, or about 320 nm. In some instances, the UV-B is administered or peaking in a range of about 280 nm to about 290 nm, about 280 nm to about 300 nm, about 280 nm to about 310 nm, about 280 nm to about 320 nm, about 290 nm to about 300 nm, about 290 nm to about 310 nm, about 290 nm to about 320 nm, about 300 nm to about 310 nm, about 300 nm to about 320 nm, or about 310 nm to about 320 nm. In some instances, the UV-B is administered or peaking in a range of 280 nm (±5 nm) to 284 nm (±5 nm), 279 nm (±5 nm) to about 288 nm, about 289 nm to about 300 nm, or 286 nm (±5 nm) to about 305 nm. In some instances, UV-B is peaking at 282 nm. In some instances, UV-B is peaking at 292 nm.

Optionally, the wavelength within the 280-310 nm range during the method treatment for a given plant species is altered. In some instances, a combination of different wavelengths within the UV-B spectrum is concurrently used.

In some instances, LED lights are configured to administer a peak irradiance wavelength of light, for instance center around 290 nm. In some instances, the light source is a LED. Often LED lights are configured to administer a peak irradiance wavelength of light, for instance at about 280 nm, a range within 10 nm, 9 nm, 8 nm, 7 nm, 6 nm, 5 nm, 4 nm, 3 nm, 2 nm, or 1 nm of 280 nm, or exactly 280 nm, at about 286 nm, a range within 10 nm, 9 nm, 8 nm, 7 nm, 6 nm, 5 nm, 4 nm, 3 nm, 2 nm, or 1 nm of 286 nm, or exactly 286 nm. Alternately, LED lights are configured to administer light at a standard white light spectrum which is supplemented by light in the UV-B range, for example at about 280 nm, a range within 10 nm, 9 nm, 8 nm, 7 nm, 6 nm, 5 nm, 4 nm, 3 nm, 2 nm, or 1 nm of 280 nm, or exactly 280 nm, at about 286 nm, a range within 10 nm, 9 nm, 8 nm, 7 nm, 6 nm, 5 nm, 4 nm, 3 nm, 2 nm, or 1 nm of 286 nm, or exactly 286 nm.

The LED lights or light source may administer light to a plant material at various distances. In some instances, the distance from the plant material and the light source is at least or about 5, 10, 15, 20, 30, 40, 50, 60, 70, 80, 90, 100, 120, 140, 160, 180, 200, or more than 200 millimeters (mm). In some instances, the distance from the plant material and the light source is in a range of about 5 to about 300, about 10 to about 200, about 20 to about 140, about 30 to about 120, or about 40 to about 60 mm. In some instances, the distance from the plant material and the light source is about 50 mm. In some instances, the distance from the plant material and the light source is about 70 mm. In some instances, the light that is administered is enriched or supplemented with UV-B.

In some instances, the light source is stationary. In some instances, the light source moves, for example, along a conveyor. In some instances, the speed of a moving light source is at least or about 20, 30, 40, 50, 60, 70, 80, 90, 100, 120, 140, 160, 180, 200, or more than 200 millimeters per second (mm/second). In some instances, the speed of a moving light source is at least or about 40, 41, 42, 43, 44, 45, 46, 47, 48, 49, 50, 51, 52, 53, 54, 55, 56, 57, 58, 59, 60, or more than 60 mm/second. In some instances, the speed of a moving light source is in a range of about 5 to about 200, about 10 to about 160, about 20 to about 100, or about 40 to about 60 mm/second. In some instances, the speed of a moving light source is about 50 mm/second. In some instances, the speed of a moving light source is about 53 mm/second.

In some instances, methods as described herein do not comprise the use of other UV wavelengths such as UV-A or UV-C in combination with the specific UV-B treatment. In some instances, other wavelengths outside of the 280-310 nm UV-B treatment do not comprise part of the methods as described herein. In some instances, there is a significant advantage over treatment methods which use multiple wavelengths in more than one spectrum.

The preferred dosage regime(s) may vary and take into account various parameters including, but not limited to, the type of seedling, the intensity of the UV light (W m$^{-2}$ s$^{-1}$), the length of treatment (days) and the rest period (on/off) between each UV application during treatment.

For instance, the length of treatment may be kept shorter to about 2-4 days, but as a result a higher intensity of UV irradiation may be used to provide a sufficient dosage during the treatment period. One consideration is that higher intensities may be more likely to lead to seedling damage, so sufficient rest periods during each application may be particularly useful. Additionally, co-administration with blue and red visible light may be particularly useful.

Additionally, it should be appreciated that the UV exposure time, timing of UV exposure to the seedling following germination, temperature, number of cycles, the particular UV wavelength may each be altered to suit different plant varieties, yet still keep within the spirit of the disclosure. Preferably, the method includes exposing the plant seedling to UV light for approximately 2-15 days. In some instances, treatment is less than 2 days. In some instances, treatment is more than 2 days. In some instances, methods as described herein comprise exposing the plant seedling or plant material to UV light for about 4 to about 7 days.

A number of UV-B administration durations are consistent with the disclosure herein. For example, a length of time of UV-B irradiation is up to 72 hours, up to 60 hours, up to 48 hours, up to 36 hours, up to 24 hours, up to 23, hours, up to 22 hours, up to 21 hours, up to 20 hours, up to 19 hours, up to 18 hours, up to 17 hours, up to 16 hours, up to 15 hours, up to 14 hours, up to 13 hours, up to 12 hours, up to 11 hours, up to 10 hours, up to 9 hours, up to 8 hours, up to 7 hours, up to 6 hours, up to 5 hours, up to 4 hours, up to 3 hours, up to 2 hours, up to 1 hour, or less than one hour. In some instances, UV-B treatment is about 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, 24 hours, 30 hours, 32 hours, 50 hours, 72 hours, or more than 72 hours. Some treatments are for less than about or at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 60 minutes, or more than 60 minutes. In some instances, UV-B administration duration is in a range of about 0 hours to about 60 hours or about 5 hours to about 30 hours. In some instances, UV-B treatment is about 1 day, 2 days, 3 days, 4 days, 5 days, 6 days, 7 days, 8 days, 9 days, 10 days, 12 days, 14 days, 16 days, 18 days, 20 days, 24 days, 30 days, 32 days, 50 days, 72 days, or more than 72 days. In some instances, UV-B treatment is in a range of about 1 day to about 30 days, about 2 days to about 25 days, about 4 days to about 20 days, about 6 days to about 18 days, or about 8 days to about 16 days. In some instances, UV-B treatment is about 5 days to about 20 days or about 2 days to about 30 days. In some instances, UV-B treatment is less than about 2 days. In some instances, UV-B treatment is more than about 30 days. In some instances, UV-B treatment is about 14 days.

UV-B administration may occur at a time before fruit is harvested. In some instances, UV-B administration occurs before a flower opens. In some instances, UV-B administration occurs before buds begin to form. In some instances, UV-B administration occurs before a first pollen release. In some instances, UV-B administration occurs before fertilization. UV-B administration may occur at a time before fruit biomass can be measured. Methods for estimating fruit biomass includes, but are not limited to, measuring counts of fruits, measuring counts of all stems of fruit producing plant material, and measuring land coverage of fruit producing plant material. In some instances, UV-B administration occurs at least or about 1 day, 2 days, 3 days, 4 days, 5 days, 6 days, 7 days, 8 days, 9 days, 10 days, 12 days, 14 days, 16 days, 18 days, 20 days, 24 days, 30 days, 32 days, 50 days, 72 days, or more than 72 days before at least one of a time that fruit is harvested, flowers are opened, buds begin to form, first pollen is released, fertilization, and fruit biomass is measured. In some instances, UV-B administration occurs at least or about 1 week, 2 weeks, 3 weeks, 4 weeks, 5 weeks, 6 weeks, 7 weeks, 8 weeks, or more before at least one of a time that fruit is harvested, flowers are opened, buds begin to form, first pollen is released, fertilization, and fruit biomass is measured.

UV-B administration may be accomplished in a single dose. In some embodiments, the UV-B administration is a single or multitude time point treatment. In cases of multitude time point treatment, UV-B administration may be separated by any appropriate interval. In some instances, UV-B administration is separated by intervals of less than, about, exactly or at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, or 60 minutes. In some instances, UV-B administration is separated by intervals of or less than, about, exactly or at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, or more than 60 hours.

In some instances, the method includes exposing the plant seedling or plant material to cyclic exposure of UV-B light. For example, the UV-B exposure is provided as about 12 hours on, 12 hours off over a period of seven days. In some instances, the UV-B exposure is provided as about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, or 23 hours on and 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, or 23 hours off. In some instances, the UV-B exposure is for a period of at least or about 1 day, 2 days, 3 days, 4 days, 5 days, 6 days, 7 days, 8 days, 9 days, 10 days, 11 days, 12 days, 13 days, or 14 days. In some instances, the UV exposure is for a period of at least or about 1 week, 2 weeks, 3 weeks, 4 weeks, 5 weeks, 6 weeks, 7 weeks, 8 weeks, or more. In another example, the UV-B exposure may be provided 10 minutes per day for a week. It should be appreciated that different conditions may suit different plant varieties and/or specific outcomes desired by the grower.

Cyclic exposure of UV-B light may comprise various numbers of cycles per day. In some instances, the number of cycles per day is at least or about 50, 100, 150, 200, 250, 300, 350, 400, 450, 500, 550, 600, 650, 700, 750, 800, 850, 900, 950, 1000, or more than 1000 cycles per day. In some instances, the number of cycles per day is in a range of about 50 to about 100, about 100 to about 900, about 200 to about 800, about 300 to about 700, or about 400 to about 600 cycles per day. In some instances, the number of cycles per day is in a range of about 380 to about 500 or about 250 to about 600 cycles per day. In some instances, the number of cycles per day is less than about 250 cycles per day. In some instances, the number of cycles per day is more than about 250 cycles per day. In some instances, the number of cycles per day is about 430 cycles per day. In some instances, the number of cycles per day is about 433 cycles per day.

In some instances, a regularity of light exposure varies. In some instances, the light is enriched or supplemented using UV-B. In some instances, the light exposure is at least or about 20, 30, 40, 50, 60, 70, 80, 90, 100, 120, 140, 160, 180, 200, 220, 240, 260, 280, 300, 320, 340, 360, 380, 400, or more than 400 seconds. In some instances, the light exposure is in a range of about 20 to about 300, about 40 to about 200, about 60 to about 140, about 80 to about 100, or about 90 to about 180 seconds. In some instances, the light exposure is less than 20 seconds. In some instances, the light exposure is more than 300 seconds. In some instances, the light exposure is about 130 seconds. In some instances, the light exposure is about 133 seconds.

Described herein are methods for administering UV-B to a plant material, wherein the method includes maintaining the temperature in a range of about 12° C. to about 35° C. during the treatment. In some instances, the temperature is maintained at least or about 5° C., 6° C., 7° C., 8° C., 9° C., 10° C., 11° C., 12° C., 13° C., 14° C., 15° C., 16° C., 17° C., 18° C., 20° C., 22° C., 24° C., 26° C., 28° C., 30° C., 32° C., 34° C., 36° C., 38° C., 40° C., or more than 40° C. The temperature may be maintained in a range of about 5° C. to about 40° C., about 10° C. to about 30° C., or about 15° C. to about 25° C. In some instances, the temperature is maintained to avoid temperature damage to the seedlings during the treatment stage.

Various dosages of UV-B are contemplated herein. In some instances, the dosage is in the range of about 0.01 kJ m$^{-2}$ to about 368 kJ m$^{-2}$. In some instances, the dosage is about 0.01 kJ m$^{-2}$–368 kJ m$^{-2}$, 0.1 kJ m$^{-2}$–300 kJ m$^{-2}$, 1 kJ m$^{-2}$–250 kJ m$^{-2}$, 10 kJ m$^{-2}$–200 kJ m$^{-2}$, 100 kJ m$^{-2}$–150 kJ m$^{-2}$, 200 kJ m$^{-2}$–300 kJ m$^{-2}$, 250 kJ m$^{-2}$–350 kJ m$^{-2}$, or 300 kJ m$^{-2}$–368 kJ m$^{-2}$. In some instances, the dosage is in the range of about 0.1 to about 12 kJ m$^{-2}$. In some instances, the dosage is about 13 kJ m$^{-2}$. The light treatment may be at a dose of about 13 kJ m$^{-2}$, exactly 13 kJ m$^{-2}$, or at least 13 kJ m$^{-2}$. In some instances, the dosage is about 37 kJ m$^{-2}$. In some instances, the dosage is about 69 kJ m$^{-2}$. In some instances, the dosage is about 78 kJ m$^{-2}$. In some instances, the dosage is about 98 kJ m$^{-2}$. In some instances, the dosage is about 100 kJ m$^{-2}$. The light treatment may be at a dose of about 100 kJ m$^{-2}$, exactly 100 kJ m$^{-2}$, or more than 100 kJ m$^{-2}$. In some instances, the dosage is about 125 kJ m$^{-2}$. In some instances, the dosage is about 204 kJ m$^{-2}$. The light treatment may be at a dose range of about 13 kJ m$^{-2}$ to 100 kJ m$^{-2}$. The UV-B can be at a dose in a range of about 1 kJ m$^{-2}$–1000 kJ m$^{-2}$, 10 kJ m$^{-2}$–800 kJ m$^{-2}$, 20 kJ m$^{-2}$–600 kJ m$^{-2}$, 30 kJ m$^{-2}$–400 kJ m$^{-2}$, 50 kJ m$^{-2}$–200 kJ m$^{-2}$, 100 kJ m$^{-2}$–150 kJ m$^{-2}$, 30 kJ m$^{-2}$–60 kJ m$^{-2}$, or 150 kJ m$^{-2}$–250 kJ m$^{-2}$. In some instances, the UV-B is in a range of 0 kJ m$^{-2}$–20 kJ m$^{-2}$, 20 kJ m$^{-2}$–40 kJ m$^{-2}$, 40 kJ m$^{-2}$–60 kJ m$^{-2}$, 60 kJ m$^{-2}$–80 kJ m$^{-2}$, or 80 kJ m$^{-2}$–100 kJ m$^{-2}$.

Various irradiances of UV-B may be used. In some cases, the irradiance is in a range of about $4 \times 10^{-5}$ W cm$^{-2}$ s$^{-1}$ to about $1.3 \times 10^{-4}$ W cm$^{-2}$ s$^{-1}$. The irradiance range can be at about $4 \times 10^{-5}$ W cm$^{-2}$ s$^{-1}$, exactly $4 \times 10^{-5}$ W cm$^{-2}$ s$^{-1}$, or at least $4 \times 10^{-5}$ W cm$^{-2}$ s$^{-1}$. In some cases, the irradiance is in a range of about $1.3 \times 10^{-4}$ W cm$^{-2}$ s$^{-1}$, exactly $1.3 \times 10^{-4}$ W cm$^{-2}$ s$^{-1}$, or more than $1.3 \times 10^{-4}$ W cm$^{-2}$ s$^{-1}$. The irradiance range can be about $4 \times 10^{-5}$ W cm$^{-2}$ s$^{-1}$-$6 \times 10^{-5}$ W cm$^{-2}$ s$^{-1}$, $6 \times 10^{-5}$ W cm$^{-2}$ s$^{-1}$-$8 \times 10^{-5}$ W cm$^{-2}$ s$^{-1}$, $8 \times 10^{-5}$ W cm$^{-2}$ s$^{-1}$-$1 \times 10^{-4}$ W cm$^{-2}$ s$^{-1}$, or $1 \times 10^{-4}$ W cm$^{-2}$ s$^{-1}$-$1.5 \times 10^{-5}$ W cm$^{-2}$ s$^{-1}$. Dosage may change in relation to treatment protocols such as hydration protocols.

In some instances, the irradiance of UV-B is at least or about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or more than 100 umol cm$^{-2}$ s$^{-1}$. In some instances, the irradiance of UV-B is in a range of about 15 to about 80, about 15 to about 25, about 16 to about 24, or about 25 to about 40 umol cm$^{-2}$ s$^{-1}$. In some instances, the irradiance of UV-B is lower than about 15 umol cm$^{-2}$ s$^{-1}$. In some instances, the irradiance of UV-B is more than about 25 umol cm$^{-2}$ s$^{-1}$. In some instances, the irradiance of UV-B is more than about 80 umol cm$^{-2}$ s$^{-1}$. In some instances, the irradiance of UV-B is about 20 umol cm$^{-2}$ s$^{-1}$. In some instances, the irradiance of UV-B is about 30 umol cm$^{-2}$ s$^{-1}$.

In some instances, when UV-B is co-administered with light of another wavelength, UV-B is enriched as compared to the light of another wavelength. In some instances, UV-B is enriched at least or about 15%, 20%, 25%, 30%, 35%, 40%, 45%, 50%, 60%, 70%, 80%, 90%, 100%, 125%, 150%, 175%, 200%, 225%, 250%, 275%, 300%, or more than 300% more than the light of another wavelength. In some instances, UV-B is supplemented. In some instances, UV-B is the predominant wavelength during light administration. In some instances, UV-B comprises at least or about 15%, 20%, 25%, 30%, 35%, 40%, 45%, 50%, 60%, 70%, 80%, 90%, 100% of light for light administration.

Described herein are methods for administering UV-B to a plant seedling or plant material, wherein the method, in some embodiments, comprises administration of visible light in the range of about 400 to about 800 nm. The visible light may be administered concurrently with the UV light, or separately. In some cases, visible light is administered at about or up to 500 umol m$^{-2}$ s$^{-1}$. In some instances, visible light is administered at about or up to 400 umol m$^{-2}$ s$^{-1}$, about or up to 300 umol m$^{-2}$ s$^{-1}$, about or up to 200 umol m$^{-2}$ s$^{-1}$, about or up to 100 umol m$^{-2}$ s$^{-1}$, about or up to 50 umol m$^{-2}$ s$^{-1}$, or about or less than 50 umol m$^{-2}$ s$^{-1}$. Often visible light is administered at about 50 umol m$^{-2}$ s$^{-1}$. In some cases, about 20 umol m$^{-2}$ s$^{-1}$ of visible light is administered. Often the visible light can have a photon number in a range of 10 m$^{-2}$ s$^{-1}$-550 m$^{-2}$ s$^{-1}$, 20 m$^{-2}$ s$^{-1}$-500 m$^{-2}$ s$^{-1}$, 40 m$^{-2}$ s$^{-1}$-450 m$^{-2}$ s$^{-1}$, 45 m$^{-2}$ s$^{-1}$-400 m$^{-2}$ s$^{-1}$, 50 m$^{-2}$ s$^{-1}$-350 m$^{-2}$ s$^{-1}$, 100 m$^{-2}$ s$^{-1}$-300 m$^{-2}$ s$^{-1}$, or 100 m$^{-2}$ s$^{-1}$-200 umol m$^{-2}$ s$^{-1}$.

Notably, visible light is not UV-light and therefore is distinguishable from prior art treatments in Behn et al and WO 2012/085336 which utilized both UV-B and UV-A in the treatment. In some instances, inclusion of visible light helps prevents any DNA damage to the plants. In some instances, inclusion of visible light helps the beneficial hardiness characteristics obtained by the UV exposure to prevail.

Described herein are methods for administering UV-B to a plant seedling or plant material, wherein the method, in some embodiments, comprises administration of blue visible light. In some instances, blue visible light helps avoid possible deleterious effects of UV damage to DNA. In some instances, blue light beneficial for photo-repair. In some instances, blue visible light or blue light is administered or is peaking in a range of about 450 (±5 nm) to about 500 nm or about 455 to about 492 nm. In some instances, blue visible light or blue light is administered or is peaking at least or about 430 nm, 435 nm, 440 nm, 445 nm, 450 nm, 455 nm, 460 nm, 465 nm, 470 nm, 475 nm, 480 nm, 485 nm, or 490 nm. In some instances, blue visible light or blue light is administered or is peaking in a range of 430 nm to 480 nm or 440 nm to 460 nm. In some instances, blue visible light or blue light is administered or is peaking at about 450 nm. In some instances, blue visible light or blue light is administered or is peaking at about 453 nm.

Irradiance of blue light includes, but is not limited to, 5, 10, 20 30, 40, 50, 60, 70, 80, 90, 100, 200, 300, 400, 500, 600, 700, 800, 900, 1000, 2000, 3000, 4000, 5000, 6000, or more than 6000 umol m$^{-2}$ s$^{-1}$. The irradiance of blue light may be in a range of about 5 to about 5000, about 5 to about 2000, about 20 to about 800, about 40 to about 600, about 60 to about 400, about 80 to about 200, about 30 to about 130, or about 33 to about 133 umol m$^{-2}$ s$^{-1}$. In some instances, the irradiance of blue light is about 60 umol m$^{-2}$ s$^{-1}$. In some instances, the irradiance of blue light is about 66 umol m$^{-2}$ s$^{-1}$.

Described herein are methods for administering UV-B to a plant seedling or plant material, wherein the method, in some embodiments, comprises administration of red visible light. In some instances, the benefits of red visible light are complementary effects on plant growth, such as regulation of stem growth. Red visible light or red light may be administered or is peaking in a range of about 655 to about 680 nm, about 620 nm to about 690 nm, or about 640 nm to about 680 nm. In some instances, red visible light or red light is administered or is peaking at 620 nm (±5 nm), about 630 nm, about 640 nm, about 660 nm, about 670 nm, about 680 nm, about 690 nm, about 700 nm, about 710 nm, about 720 nm, about 730 nm, about 740 nm, or about 750 nm (±5 nm). In some instances, red visible light or red light is administered or is peaking at about 660 nm. In some instances, red visible light or red light is administered or is peaking at about 659 nm.

Irradiance of red light includes, but is not limited to, 5, 10, 20 30, 40, 50, 60, 70, 80, 90, 100, 200, 300, 400, 500, 600, 700, 800, 900, 1000, 2000, 3000, 4000, 5000, 6000, or more than 6000 umol m$^{-2}$ s$^{-1}$. The irradiance of red light may be in a range of about 5 to about 5000, about 30 to about 3000, about 20 to about 800, about 40 to about 600, about 60 to about 400, about 66 to about 266, about 70 to about 300, about 80 to about 200, or about 30 to about 130 umol m$^{-2}$ s$^{-1}$. In some instances, the irradiance of red light is about 130 umol m$^{-2}$ s$^{-1}$. In some instances, the irradiance of red light is about 133 umol m$^{-2}$ s$^{-1}$.

Also, the treatment conditions may depend on the type of device that is utilized, as a particular device may be particularly efficient at administering the UV light.

Various treatment conditions and combinations of treatments described previously may be used. The treatment conditions may comprise, but are not limited to, treatment distance from plant to light source (mm), speed of moving light source (mm/second), light source timing cycles (regularity of each exposure, seconds), number of cycles per day, irradiance of UV-B (umol cm$^{-2}$ s$^{-1}$), peak wavelength of UV-B, irradiance of red light (umol m$^{-2}$ s$^{-1}$), peak wavelength of red light (nm), irradiance of blue light (umol m$^{-2}$ s$^{-1}$), peak wavelength of blue light (nm), and total days of treatment. In some instances, treatment conditions may comprise 1 condition, 2 conditions, 3 conditions, 4 conditions, more than 4 conditions, and permutations and combinations thereof. For example, the treatment condition comprises various distances of a light source to a plant material. In some instances, the distance from the plant material and the light source is in a range of about 5 to about 200, about 10 to about 160, about 20 to about 140, about 30 to about 120, or about 40 to about 60 mm. In some instances, the distance from the plant material and the light source is about 50 mm. In some instances, the distance from the plant material and the light source is about 70 mm. In some instances, the treatment condition comprises movement of a light source. In some instances, the speed of a moving light source is at least or about 20, 30, 40, 50, 60, 70, 80, 90, 100, 120, 140, 160, 180, 200, or more than 200 millimeters per second (mm/second). In some instances, the speed of a moving light source is in a range of about 5 to about 200, about 10 to about 160, about 20 to about 100, or about 40 to about 60 mm/second. In some instances, the speed of a moving light source is about 53 mm/second. In some instances, the light source administers UV-B. In some instances, the treatment condition comprises cyclic exposure of UV-B light. In some instances, cyclic exposure of UV-B light comprises at least or about 50, 100, 150, 200, 250, 300, 350, 400, 450, 500, 550, 600, 650, 700, 750, 800, 850, 900, 950, 1000, or more than 1000 cycles per day. In some instances, the number of cycles per day is more than about 250 cycles per day. In some instances, the number of cycles per day is about 433 cycles per day. In some instances, the treatment condition comprises administration of light enriched or supplemented with UV-B. In some instances, the UV-B is administered or peaking in a range of about 280 nm to about 290 nm, about 280 nm to about 300 nm, about 280 nm to about 310 nm, about 280 nm to about 320 nm, about 290 nm to about 300 nm, about 290 nm to about 310 nm, about 290 nm to about 320 nm, about 300 nm to about 310 nm, about 300 nm to about 320 nm, or about 310 nm to about 320 nm. In some instances, the UV-B is administered or peaking in a range of 280 nm (±5 nm) to 284 nm (±5 nm), 279 nm (±5 nm) to about 288 nm, about 289 nm to about 300 nm, or 286 nm (±5 nm) to about 305 nm. In some instances, UV-B is peaking at 282 nm. In some instances, UV-B is peaking at 292 nm. In some instances, the treatment condition comprises various durations of UV-B treatment. In some instances, UV-B treatment is about 1 day, 2 days, 3 days, 4 days, 5 days, 6 days, 7 days, 8 days, 9 days, 10 days, 12 days, 14 days, 16 days, 18 days, 20 days, 24 days, 30 days, 32 days, 50 days, 72 days, or more than 72 days. In some instances, UV-B treatment is in a range of about 1 day to about 30 days, about 2 days to about 25 days, about 4 days to about 20 days, about 6 days to about 18 days, or about 8 days to about 16 days. The treatment condition may be light exposure. In some instances, the light exposure is at least or about 20, 30, 40, 50, 60, 70, 80, 90, 100, 120, 140, 160, 180, 200, 220, 240, 260, 280, 300, 320, 340, 360, 380, 400, or more than 400 seconds. In some instances, the light exposure is in a range of about 20 to about 300, about 40 to about 200, about 60 to about 140, about 80 to about 100, or about 90 to about 180 seconds. In some instances, the light exposure is about 133 seconds. The light exposure may comprise light enriched or supplemented with UV-B. In some instances, the treatment condition comprises various irradiances of UV-B. In some instances, the irradiance of UV-B is at least or about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or more than 100 umol cm$^{-2}$ s$^{-1}$. In some instances, the irradiance of UV-B is in a range of about 15 to about 80, about 15 to about 25, or about 25 to about 40 umol cm$^{-2}$ s$^{-1}$. In some instances, the irradiance of UV-B is about 20 umol cm$^{-2}$ s$^{-1}$. In some instances, the irradiance of UV-B is about 30 umol cm$^{-2}$ s$^{-1}$. Treatment conditions may also comprise administration of at least one of blue light and red light. In some instances, blue visible light or blue light is administered or is peaking at least or about 430 nm, 435 nm, 440 nm, 445 nm, 450 nm, 455 nm, 460 nm, 465 nm, 470 nm, 475 nm, 480 nm, 485 nm, or 490 nm. In some instances, blue visible light or blue light is administered or is peaking in a range of 430 nm to 480 nm or 440 nm to 460 nm. In some instances, blue visible light or blue light is administered or is peaking at about 453 nm. Irradiance of blue light includes, but is not limited to, 5, 10, 20 30, 40, 50, 60, 70, 80, 90, 100, 200, 300, 400, 500, 600, 700, 800, 900, 1000, 2000, 3000, 4000, 5000, 6000, or more than 6000 umol m$^{-2}$ s$^{-1}$. In some instances, irradiance of blue light is about 66 umol m$^{-2}$ s$^{-1}$. In some instances, red visible light or red light is administered or is peaking at 620 nm (±5 nm), about 630 nm, about 640 nm, about 660 nm, about 670 nm, about 680 nm, about 690 nm, about 700 nm, about 710 nm, about 720 nm, about 730 nm, about 740 nm, or about 750 nm (±5 nm). In some instances, red visible light or red light is administered at or is peaking at about 659 nm. Irradiance of red light includes values of 5, 10, 20 30, 40, 50, 60, 70, 80, 90, 100, 200, 300, 400, 500, 600, 700, 800, 900, 1000, 2000, 3000, 4000, 5000, 6000, or more than 6000 umol m$^{-2}$ s$^{-1}$. In some instances, irradiance of red light is about 133 umol m$^{-2}$ s$^{-1}$.

Application to different types of seedlings and plant materials Application to a number of plant materials is consistent with the disclosure herein. Exemplary plant materials subjected to treatments herein include plant seedlings or other materials, such as runners, post-seedling plants, leaves, roots, shoot meristems, whole plant application, such as whole plants grown hydroponically or aeroponically. In some cases plant material is selected from the group consisting of fruit and vegetables. In some instances, the plant seedling or plant material is selected from the group consisting of green lettuce, red lettuce, tomato, cucumber, broccoli, herb crops, *cannabis*, strawberry and eggplant. In some instances, the plant material is from at least one of tomato, strawberry, and *cannabis*. In some instances, the plant seedling or plant material is a commercially important crop. The method may also be applicable to a wide variety of other crop types without limitation.

Described herein are methods and devices for administration of light enriched or supplemented with UV-B to a crop plant. In some instances, the crop plant is a fruiting plant. In some instances, the crop plant is a plant in the family Rosaceae. In some instances, the Rosaceae plant is of genus *Fragaria*. The crop plant may be of a species including, but not limited to, *Fragaria chiloensis, Fragaria daltoniana, Fragaria glauca, Fragaria iinumae, Fragaria iturupensis, Fragaria moschata, Fragaria moupinensis, Fragaria nilgerrensis, Fragaria nipponica, Fragaria nipponica yakusimensis, Fragaria nubicola, Fragaria orientalis, Fragaria vesca, Fragaria virginiana, Fragaria viridis, Fragaria yezoensis, Fragaria×ananassa, Fragaria×Comarum*, and *Fragaria×vescana*. In some instances, the plant is a strawberry plant. In some instances, the strawberry plant is at least one of a June-bearing, everbearing, and day-neutral strawberry plant.

Methods and devices as described herein may be administered to a plant material. In some instances, the plant material is a runner. In some instances, the plant material is a seed. In some instances, the plant material is a seedling. In some instances, the plant material is a growing plant that has developed past a seedling stage, such as through the development or reliance upon post-embryonic tissues for the majority of its photosynthesis.

UV-B may be administered at a propagation stage of the plant material. In some instances, the propagation stage comprises runners. In some instances, the propagation stage comprises shoots. In some instances, the propagation stage comprises cuttings.

Various cultivation systems for use with methods and devices as described herein may be used. For example, the plant material is grown in soil. In some instances, the plant material is grown using hydroponics or aeroponics. Plants are grown in controlled greenhouse conditions, such as conventional greenhouse conditions or vertical farming conditions. Alternately, plants are grown outdoors.

Device

A number of devices are consistent with the implementation of the methods and treatment recipes as disclosed herein. In some instances, the device has the ability to administer a pre-defined UV dosage regime such as those described in the present application and wherein parameters preferably used in the present disclosure may be easily adjusted and controlled.

In some instances, the device includes a moving conveyor which alters the relative position of at least one light emitter and the target area during the treatment. In this way a large number of plant seedlings may be conveniently and accurately treated during the treatment phase as the conveyor moves the position of the light emitters.

In some instances, the device administers UV light according to the present disclosure via light emitting diodes (LEDs).

In some instances, the device is configured to co-administer visible light with UV light, which is beneficial for the reasons discussed above.

Some such devices are configured to administer various treatment conditions and combinations of treatments as described herein. For example, the device controls at least one of treatment distance from plant to light source (mm), speed of moving light source (mm/second), light source timing cycles (regularity of each exposure, seconds), number of cycles per day, irradiance of UV-B (umol cm$^{-2}$ s$^{-1}$), peak wavelength of UV-B, irradiance of red light (umol m$^{-2}$ s$^{-1}$), peak wavelength of red light (nm), irradiance of blue light (umol m$^{-2}$ s$^{-1}$), peak wavelength of blue light (nm), and total days of treatment.

In some instances, the device is configured to regulate or to hold its light source at a fixed or otherwise determined distance of a light source to a plant material. In some instances, the distance from the plant material and the light source is in a range of about 5 to about 200, about 10 to about 160, about 20 to about 140, about 30 to about 120, or about 40 to about 60 mm. In some instances, the distance from the plant material and the light source is about 50 mm. In some instances, the distance from the plant material and the light source is about 70 mm.

In some instances, the device controls a movement of a light source. In some instances, the speed of a moving light source is at least or about 20, 30, 40, 50, 60, 70, 80, 90, 100, 120, 140, 160, 180, 200, or more than 200 millimeters per second (mm/second). In some instances, the speed of a moving light source is in a range of about 5 to about 200, about 10 to about 160, about 20 to about 100, or about 40 to about 60 mm/second. In some instances, the speed of a moving light source is about 50 mm/second.

Devices herein are configured to administer UV light, alone or in combination with visible light, at a range of wavelengths consistent with wavelength disclosures throughout the present disclosure, such as UV-B at or peaking in a range of about 280 nm to about 290 nm, about 280 nm to about 300 nm, about 280 nm to about 310 nm, about 280 nm to about 320 nm, about 290 nm to about 300 nm, about 290 nm to about 310 nm, about 290 nm to about 320 nm, about 300 nm to about 310 nm, about 300 nm to about 320 nm, or about 310 nm to about 320 nm. In some instances, the UV-B is administered or peaking in a range of 280 nm (±5 nm) to 284 nm (±5 nm), 279 nm (±5 nm) to about 288 nm, about 289 nm to about 300 nm, or 286 nm (±5 nm) to about 305 nm. In some instances, UV-B is peaking at 282 nm. In some instances, UV-B is peaking at 292 nm.

Devices herein are configured for continuous, single administration or regular repeating light such as cyclic exposure of UV-B light. In some instances, cyclic exposure of UV-B light comprises at least or about 50, 100, 150, 200, 250, 300, 350, 400, 450, 500, 550, 600, 650, 700, 750, 800, 850, 900, 950, 1000, or more than 1000 cycles per day. In some instances, the number of cycles per day is more than about 250 cycles per day. In some instances, the number of cycles per day is about 430 cycles per day.

Devices are often configured to administer a set duration of treatment. For example, UV-B treatment is about 1 day, 2 days, 3 days, 4 days, 5 days, 6 days, 7 days, 8 days, 9 days, 10 days, 12 days, 14 days, 16 days, 18 days, 20 days, 24 days, 30 days, 32 days, 50 days, 72 days, or more than 72 days. In some instances, UV-B treatment is in a range of about 1 day to about 30 days, about 2 days to about 25 days, about 4 days to about 20 days, about 6 days to about 18 days, or about 8 days to about 16 days. In some instances, the device controls light exposure. In some instances, the light exposure is at least or about 20, 30, 40, 50, 60, 70, 80, 90, 100, 120, 140, 160, 180, 200, 220, 240, 260, 280, 300, 320, 340, 360, 380, 400, or more than 400 seconds. In some instances, the light exposure is in a range of about 20 to about 300, about 40 to about 200, about 60 to about 140, about 80 to about 100, or about 90 to about 180 seconds. The light exposure may comprise light enriched or supplemented with UV-B.

Devices as described herein may be configured to administer a specified dosage or irradiance of light. For example, the device is configured to administer various irradiances of UV-B. In some instances, the irradiance of UV-B is at least or about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or more than 100 umol cm$^{-2}$ s$^{-1}$. In some instances, the irradiance of UV-B is in a range of about 15 to about 80, about 15 to about 25, or about 25 to about 40 umol cm$^{-2}$ s$^{-1}$.

The device may be configured to administer UV-B alone or UV-B in conjunction with at least one of blue light and red light. In some instances, the blue light is administered or is peaking at least or about 430 nm, 435 nm, 440 nm, 445 nm, 450 nm, 455 nm, 460 nm, 465 nm, 470 nm, 475 nm, 480 nm, 485 nm, or 490 nm. In some instances, blue light is administered or is peaking in a range of 430 nm to 480 nm or 440 nm to 460 nm. In some instances, blue visible light or blue light is administered or is peaking at about 450 nm. Irradiance of blue light includes, but is not limited to, 5, 10, 20 30, 40, 50, 60, 70, 80, 90, 100, 200, 300, 400, 500, 600, 700, 800, 900, 1000, 2000, 3000, 4000, 5000, 6000, or more than 6000 umol m$^{-2}$ s$^{-1}$. In some instances, red visible light or red light is administered or is peaking at 620 nm (±5 nm), about 630 nm, about 640 nm, about 660 nm, about 670 nm, about 680 nm, about 690 nm, about 700 nm, about 710 nm, about 720 nm, about 730 nm, about 740 nm, or about 750 nm (±5 nm). In some instances, red visible light or red light is administered or is peaking at about 660 nm. Irradiance of red light includes, but is not limited to, 5, 10, 20 30, 40, 50, 60, 70, 80, 90, 100, 200, 300, 400, 500, 600, 700, 800, 900, 1000, 2000, 3000, 4000, 5000, 6000, or more than 6000 umol m$^{-2}$ s$^{-1}$.

Methods to Quantify or Predict Hardiness and/or Improved Crop Yield or Quality

There are a range of methods that can be used to evaluate young plants, but that no single and fully effective method currently exists, particularly as related to the use of UV light to promote yield and/or quality in crops at harvest, as described herein.

Plant performance in plant material treated using methods as described herein may result in improved plant performance as compared to the counterpart plant material that has not been treated. In some instances, hardiness of the plant material is improved using methods as described herein. In some instances, plant performance comprises at least one of flavonoid levels, anthocyanin levels, size, dry weight, nitrogen index, shoot dry weight, shoot fresh weight, shoot length, radical length, pigment production, leaf size, hypocotyl length, chlorophyll level, leaf area, and root dry weight. In some instances, plant performance is yield. In some instances, yield is at least one of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. In some instances, yield is fruit fresh weight. In some instances, yield is Brix content. In some instances, yield is number of fruit harvested. In some instances, yield is branching. In some instances, yield is number of flowering parts.

In some instances, methods and devices as described herein result in improved yield as determined by an increase in number of fruit harvested. In some instances, methods and devices described herein result in at least or about 3000, 4000, 5000, 6000, 7000, 8000, 9000, 10000, 12000, 14000, 16000, 18000, 20000, 24000, 28000, 32000, 36000, 40000, 50000, 60000, 80000, 100000, or more than 100000 pounds of fruit harvested per acre. In some instances, methods and devices described herein result in a range of about 3000 to about 100000, about 4000 to about 80000, about 6000 to about 60000, about 10000 to about 40000, or about 20000 to about 30000 pounds of fruit harvested per acre. In some instances, methods and devices described herein result in more than 50000 pounds harvested per acre. In some instances, methods and devices described herein result in at least or about 3000, 4000, 5000, 6000, 7000, 8000, 9000, 10000, 12000, 14000, 16000, 18000, 20000, 24000, 28000, 32000, or more than 32000 trays per acre. In some instances, each try comprises about 9.5 pounds to about 10 pounds.

In some instances, methods and devices as described herein result in improved yield as determined by an increase in average fruit biomass. In some instances, methods and devices described herein result in at least or about 0.1, 0.2, 0.25, 0.3, 0.4, 0.5, 0.6, 0.7, 0.8, 0.9, 1.0, 1.25, 1.5, 1.75, 2.0, 2.25, 2.5, 2.75, 3.0, 3.5, 4.0, 5.0, or more than 5.0 pounds of fruit per foot of row. In some instances, methods and devices described herein result in a range of about 0.1 to about 5.0, about 0.2 to about 4.0, about 0.3 to about 3.5, about 0.4 to about 3.0, about 0.5 to about 2.5, or about 0.75 to about 2 pounds of fruit per foot of row. In some instances, the fruit is tomato, strawberry, or *cannabis*. In some instances, the fruit is strawberry.

In some instances, yield is improved by a significant percentage when compared to a counterpart plant material that has not been irradiated with a UV-B regimen disclosed herein. Yield may be improved by about 5%-100%, 10%-90%, 20%-80%, 30%-70%, 40%-60%, 50%-95%, 65%-85%, or 75%-95%. Yield may be improved by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100%. Yield may be improved by at least or about 5%. Yield may be improved by at least or about 10%. Yield may be improved by at least or about 30%. Yield may be improved by at least or about 50%.

Improved yield, in some instances, occurs following administration of light enriched or supplemented with UV-B. In some instances, improved yield occurs at least or about 1 day, 2 days, 3 days, 4 days, 5 days, 6 days, 7 days, 8 days, 9 days, 10 days, 12 days, 14 days, 16 days, 18 days, 20 days, 24 days, 30 days, 32 days, 50 days, 72 days, or more than 72 days following administration of light enriched or supplemented with UV-B. In some instances, improved yield occurs at least or about 1 week, 2 weeks, 3 weeks, 4 weeks, 5 weeks, 6 weeks, 7 weeks, 8 weeks, 9 weeks, 10 weeks, 11 weeks, 12 weeks, or more than 12 weeks following administration of light enriched or supplemented with UV-B.

Improved yield may be measured by resistance to infection. Infection may be caused by organisms including, but not limited to, fungi, oomycetes, bacteria, viruses, viroids, virus-like organisms, phytoplasmas, protozoa, nematodes and parasitic plants. In some cases, following UV-B treatment of the plant material as described in the methods herein, yield is unaffected or improved despite infections caused by such organisms. In some cases, following UV-B treatment of the plant material as described in the methods herein, yield is improved despite infections caused by such organisms as compared to non-UV-B irradiated plant material. In some cases, yield is inspected for infections caused by such organisms. Often yield is inspected for at least one of leaf disease, ear rot disease, stalk rot disease, and seeding and root disease.

In some instances, improved yield is measured by at least one of a reduction in fertilizer, herbicide, insecticide, and pesticide use without affecting crop yield. Reduction to fertilizer, herbicide, insecticide, or pesticide use may be determined by comparison to the industry use for a crop over ten years, to the state-wide average, or the national average. The reduction of fertilizer, use may be at least 5%. In some cases, the reduction of fertilizer is in the range of about 5%-100%, 10%-90%, 20%-80%, 30%-70%, 40%-60%, 50%-95%, 65%-85%, or 75%-95%. In some instances, the reduction of herbicide use is at least 5%. In some cases, the reduction of herbicide is in the range of about 5%-100%, 10%-90%, 20%-80%, 30%-70%, 40%-60%, 50%-95%, 65%-85%, or 75%-95%. In some instances, the reduction of insecticide use is at least 5%. In some cases, the reduction of insecticide is in the range of about 5%-100%, 10%-90%, 20%-80%, 30%-70%, 40%-60%, 50%-95%, 65%-85%, or 75%-95%. In some instances, the reduction of pesticide use is at least 5%. In some cases, the reduction of pesticide is in the range of about 5%-100%, 10%-90%, 20%-80%, 30%-70%, 40%-60%, 50%-95%, 65%-85%, or 75%-95%.

Accordingly, UV-B supplementation or enrichment enables methods of growing crops such that pesticide use, herbicide use, fertilizer administration, or water administration may be reduced relative to untreated plant material without any concomitant decrease in yield. In some cases, UV-B supplementation enables a substantial decrease in overall environmental impact without decrease in crop yield.

Improvements yield may be determined by comparison of UV-B irradiated plant material to non-UV-B irradiated plant material. In some instances, improvements in yield is determined in the resultant crops from UV-B irradiated plant material that are compared to crops grown under similar conditions but from plant material that are not administered UV-B using methods described herein. Similar conditions may be similar environment or similar growing conditions. Environmental factors include, but are not limited to, sun exposure, temperature, soil composition, soil moisture, wind, humidity, and soil pH. Growing conditions, include but are not limited to, amount of watering, amount of pesticide, amount of herbicide, amount of insecticide, duration of priming, duration of germination, and timing of sowing. In some instances, the resultant crops are compared to crops grown at a same time. For example, the crops grown at the same time are grown on an adjacent or nearby field. In some instances, the resultant crops are compared to crops from a previous growing season. In some instances, a yield of the resultant crops is compared to a comparable crop. In some instances, yield from a comparable crop is referred to standard yield. In some instances, the comparable crop is a crop that is grown at a same time or subject to similar growing conditions.

Improvements yield may be determined by comparison of a field comprising UV-B irradiated plant material to a field comprising non-UV-B irradiated plant material. In some instances, improvements in yield is determined in the resultant crops of a field from UV-B irradiated plant material that are compared to a field comprising crops grown under similar conditions but from plant material that are not administered UV-B using methods described herein. Similar conditions may be similar environment or similar growing conditions. Environmental factors include, but are not limited to, sun exposure, temperature, soil composition, soil moisture, wind, humidity, and soil pH. Growing conditions, include but are not limited to, amount of watering, amount of pesticide, amount of herbicide, amount of insecticide, duration of priming, duration of germination, and timing of sowing. In some instances, the field comprising UV-B irradiated plant material is compared to the field comprising non-UV-B irradiated plant material grown at a same time. The fields may be adjacent fields or nearby fields. The fields may be fields of comparable size. In some instances, the field comprising UV-B irradiated plant material is compared to a field comprising non-UV-B irradiated plant material from a previous growing season. In some instances, the field comprising UV-B irradiated plant material is compared to a historical average of fields comprising non-UV-B irradiated plant material. In some instances, the field comprising UV-B irradiated plant material is compared to an expected average yield for a field comprising non-UV-B irradiated plant material. In some instances, the expected average yield for a field is based on a national average. In some instances, the expected average yield for a field is based on a historical average for a particular growing region.

An exemplary method to evaluate the benefits of the disclosure is a "Hardiness index" as described below in detail. This is an integrated method for assessing the response of seedlings to UV light, as related to key combined physiological changes in plants in response to the treatment. In other words, the observation of several key physiological responses which have occurred simultaneously is one indication that plants have responded to treatment in a manner which should be beneficial for long term plant growth and subsequently improved crop yield and/or quality.

It should be appreciated that seedlings of different crop type, variety, and growing location may require amended hardiness indices, in order to fully assess hardiness in those particular seedlings. Amendments to the hardiness index may include the integration of other seedling or growing environment variables as required.

Hardiness Index

Throughout this specification the term hardiness index is defined according to the calculation provided below, $$H = \frac{SDW^T}{SDW^N} + \frac{SSLW^T}{SSLW^N} + \frac{1/SLA^T}{1/SLA^N}$$

wherein:
H=Hardiness
SDW=Shoot dry weight
SSLW=Shoot specific leaf weight
SLA=Shoot leaf area
$^T$=Treated plants; and
$^N$=Non treated plants.

The shoot specific leaf weight (SSLW) defines the ratio of the dry weight of the leaf per unit leaf area, whereas the term shoot leaf area (SLA) simply defines the leaf area.

Furthermore, it should be appreciated that the use of the "1/SLA" function may be merely to provide a positive H value for ease of reference, and is not essential to the disclosure.

Without this 1/SLA function, the H value may be more difficult (but not impossible) to comprehend in certain circumstances. This is because the H value may, in some cases, decrease with improved hardiness. This result may arise when the plant's shoot leaf area (SLA) increases as a result of UV exposure according to the present disclosure. This increase in SLA may be seen as an improvement to hardiness in some plant varieties.

Yet, in other plant varieties, UV treatment may lead to an increase in SLA, which may actually increase hardiness in that variety. In such a case, it may be beneficial to adapt the Hardiness index as shown below, such that the SLA is not 1/SLA.

$$H = \frac{SDW^T}{SDW^N} + \frac{SSLW^T}{SSLW^N} + \frac{SLA^T}{SLA^N}$$

Regardless, it is clear the hardiness index may be adapted and may be able to account for these differences in plant varieties.

For instance, plant seedlings with a H value between 3.01 to 15 could be identified as those which are displaying increased hardiness following treatment.

The lower H value of 3.01 reflects that each of the three values should display a value of over equal to or over 1, reflecting a positive change to the plant seedling as a result of UV treatment. Therefore, an H value of 15 represents a very significant improvement or prediction for plant hardiness.

A range of H values between 3.01 to 15 is considered to be beneficial because this range corresponds to overall plant characteristics that are more likely to withstand typical stresses in the outdoor environment.

Even small increases in the H value may mean comparatively large increases in relative hardiness characteristics. For example, an increase in the H value by 0.1, indicates a 10% increase in relative hardiness.

It should be appreciated that measuring the H value typically requires destruction of the plant seedling. Therefore, individual test seedlings from a batch may be used to determine a representative H value for the batch before selecting batches or individual plant seedlings from a batch.

In some instances, hardiness comprises improved resilience following at least one of heat, flood, drought, frost, unusual climate events, salinity stress, and high visible light stress. In some instances, improved resilience in plant seedling or plant material UV-B irradiated comprises ability to germinate despite exposure to stress. In some instances, the plant seedling or plant material are inspected following at least one of heat, flood, drought, frost, unusual climate events, salinity stress, and high visible light stress.

Hardiness in seedlings or plant material irradiated with UV-B may be increased by a significant percentage when compared to counterpart seedlings or plant material that have not been irradiated with a UV-B regimen disclosed herein. Hardiness may be increased by about 5%-100%, 10%-90%, 20%-80%, 30%-70%, 40%-60%, 50%-95%, 65%-85%, or 75%-95%. Hardiness may be increased by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100%. Hardiness may be increased by at least or about 5%. Hardiness may be increased by at least or about 10%. Hardiness may be increased by at least or about 30%. Hardiness may be increased by at least or about 50%.

Additional methods to evaluate or predict hardiness and/or yield of crop at harvest include, but are not limited to, relative growth rate, or "RGR" (change in growth parameter between a first and second time point, divided by days between time points, expressed relative to original size at first time point (this is often used to measure the actual crop yield at the point of harvest), incorporation of increases in leaf phenolic chemical content; incorporation of increases in seedling photosynthetic health; and/or incorporation of reduction of seedling hypocotyl length.

In some instances, methods treatments as described herein and the use of the hardiness index and/or RGR are used to measure the beneficial outcomes in relation to hardiness and/or subsequent increased crop yield or quality. In some instances, the methodology allows mechanisms for selecting seedlings or related seedlings undergoing the same or similar UV treatment for a subsequent growth phase or using a particular UV-dosage regime for subsequent seedling treatments. For example, seedlings shown to first have an increased hardiness index often then go on to provide an increase in crop yield and quality. Alternatively, subsequent treatments may be fine-tuned depending on the RGR of preliminary trials to further improve results.

Provided herein are methods comprising using UV-B in a specific wavelength range to provide the beneficial results. In some instances, the method is seen to beneficially improve crop yield and/or quality across a wide range of plants. In some instances, the method is seen to increase seedling dry weight, increase in leaf weight or specific leaf weight and/or decreases in leaf area. In some instances, the method also appears to protect the plants against stresses including weather damage, disease and insect pest attack that may otherwise be detrimental in vulnerable plants. In some instances, the method is seen to work well with a wide variety of plants in preliminary studies.

Definitions

Unless defined otherwise, all technical and scientific terms used herein have the same meaning as is commonly understood by one of skill in the art to which this disclosure belongs. All patents and publications referred to herein are incorporated by reference.

As used in the specification and claims, the singular form "a", "an" and "the" includes plural references unless the context clearly dictates otherwise.

The term "including" is used to mean "including but not limited to." "Including" and "including but not limited to" are used interchangeably.

The term "comprising" or "comprise" as used herein is intended to refer to an open-ended set, such that a claim or list 'comprising' an element is not precluded from also reciting additional elements not listed.

The term "seed for sowing" as used herein refers to any embryonic plant prior to, and/or intended to be used for, planting to grow any form of plant life or crop for subsequent use (typically, but not solely, for human and animal consumption). Substantially any type of seed may be used according to the present disclosure, of which there are currently about 35,000 types currently known worldwide, as noted in U.S. Pat. No. 8,001,722. Results indicated that UV-B treatment of seeds improved plant performance that is extendable to any plant species.

Some non-limiting examples of seeds for are seeds of agricultural or ornamental plants, such as lettuce, beans, broccoli, cabbage, carrot, cauliflower, cucumber, melon, onion, peas, peppers, pumpkin, spinach, squash, sweetcorn, tomato, watermelon, alfalfa, canola, corn, cotton, sorghum, soybeans, sugarbeets, wheat, mint, sunflowers, or other agriculturally or ornamentally relevant plant species.

The term "seed" refers to an embryonic plant enclosed in a protective outer covering. The formation of the seed is part of the process of reproduction in seed plants, the spermatophytes, including gymnosperm and angiosperm plants. Seeds are the product of the ripened ovule, after fertilization by pollen and some growth within the mother plant. The embryo is developed from the zygote and the seed coat from the integuments of the ovule.

The term "seed germination" refers to a process by which a seed embryo develops into a seedling. It involves the activation of the metabolic pathways that lead to growth, and the emergence of the radicle or seed root and plumule or shoot. In general, seed germination is initiated through stratification, which varies among plant species according to their original ecological setting. Often though not uniformly, seed germination is triggered through a three-phase process involving water imbibition, lag phase, and radicle emergence. Seed germination may be affected by environmental conditions including, but not limited to, water, oxygen, temperature, and light.

The term "plant performance" as used herein refers to improving at least one of resilience and growth. Resilience, as used herein refers to biotic or abiotic environmental stress, which can impact the seed, the seedling, the resulting plant, the resultant crop before or after harvesting. 'Growth' generally refers to performance in the absence of an abiotic or biotic stress, such as performance under healthy or 'best case scenario' growth conditions. One observes that, depending upon growth conditions, both increase resilience and improvements in growth can result in increases in yield, depending upon growth conditions. One observes that improving both growth and resilience has the effect of improving yield of harvestable crop material relative plants resulting from untreated seeds independent of growth conditions. Plant performance also refers in some cases to improving quality of harvestable crop material, such that plant value is increased per unit yield even if yield, more coarsely defined, is unaffected. Some non-limiting examples of improved stress resilience are improved drought resistance, salinity stress, transplantation shock, long-term hardiness, high visible light stress, insect pest stress, fungal or bacterial stress, or other disease-related stress. The term "crop productivity" may in some cases be used interchangeably with "plant performance."

The term "long-term hardiness" or "hardiness" as used herein refers to the ability of a plant to withstand one or more stresses during crop production and to allow desirable yield and/or quality of the plant at harvesting. Some non-limiting examples of how improved yield is measured include weight of harvestable crop material, such as lettuce leaves, soybeans, tomato fruit, in comparison to harvestable crop material where the seeds for sowing were not treated with UV-B. Other examples of how improved yield are measured include fresh shoot weight or whole plant dry weight, improved germination of seeds resulting from the treatment method, and improved water use efficiency of the resulting plant. In some cases, improved quality is assessed as a quantitative or qualitative assessment of at least one of a lack of blemishes on the crop (either internal or on the surface, typically from insects), improved shelf life, improved resistance to bruising or other post-harvest handling, lack of deformities, lack of irregular shapes, lack of irregular sizes, improved taste, size, shape, color, and texture. An advantage of the present disclosure is that both stress resilience and plant yield were observed (often these traits can work in an inverse relationship, where resilience is achieved at the cost of yield as seen with UV-C treatment).

The term "ultraviolet (UV) irradiation" as used herein refers to electromagnetic radiation with a wavelength shorter than visible light, but longer than X-rays, and is in between the range of 10 nm to 400 nm (corresponding to 3 eV to 124 eV). The UV radiation spectrum is considered to be invisible to humans, and therefore differentiated from visible light in the spectrum of about 400 nm to 700 nm.

The term "UV-B radiation" as used herein refers to radiation specifically within the waveband of 320 nm to 280 nm (herein described as the UV-B range). This is distinguishable from the UV-C waveband (280 to 100 nm) and UV-A waveband (400-320 nm). It should also be distinguishable from natural sunlight which although provides UV-B radiation, also includes other UV radiation. In some cases, the UV-B radiation is administered via LED lights.

The term "harvestable crop material" as used herein refers to any material from the plant which may be harvested to be used for subsequent purposes or human or animal consumption. Often the crop material is harvested seeds to be consumed as food or used for subsequent planting or breeding purposes. The harvested material includes but is not limited to a fruit, a vegetable, a tree, a shrub, a grass, a herb, and an extract or component of any one of the above crop materials. In some cases, the present disclosure is the material that is actually harvested or the material used to build plant performance without any harvesting. A non-limiting example of material not intended to be farmed is forest regeneration. Some non-limiting examples of harvestable crop material are lettuce, beans, broccoli, cabbage, carrot, cauliflower, cucumber, melon, onion, peas, peppers, pumpkin, spinach, squash, sweetcorn, tomato, watermelon, alfalfa, canola, corn, cotton, sorghum, soybeans, sugarbeets, wheat and combinations thereof.

A "fruit" refers strictly to any seed-containing organ of a plant. More informally, the term in some cases refers to harvestable material generally.

The term "flavonoid" as used herein refers to a class of plant secondary metabolites which have the general structure of a 15-carbon skeleton, consisting of two phenyl rings and heterocyclic ring (C6-C3-C6). Flavonoids are associated in some cases with stress resistance, such that an increase in their accumulation levels corresponds to an increase in plant stress resistance.

The terms "improved crop yield", "improved growth", "improved plant performance" or "improved hardiness" are used interchangeably herein. They refer to a plant which may have either larger fruit, larger stems, larger leafs, larger flowers or any combination of the above. The tissue of the enlarged plant is at least 1%, 2%, 3%, 4%, 5%, 6%, 7%, 8%, 9%, 10%, 15%, 20% 30, 40%, 50%, 60%, 70%, 80%, 90%, 99% or larger than that of a wild type plant.

The term "light intensity" refers herein to measurement of light described herein including but not limited to radiant intensity, luminous intensity, irradiance, radiance, intensity, brightness, luminance, photometry, and radiometry.

The term "radiant intensity" refers to a radiometric quantity measured in watts per steradian (W/sr).

The term "luminous intensity" refers to a photometric quantity measured in lumens per steradian (lm/sr), or candela (cd).

The term "irradiance" refers to a radiometric quantity, measured in watts per meter squared (W/m$^2$).

The term "radiance" refers to intensity (W·sr$^{-1}$·m$^{-2}$).

The term "luminance" refers to the photometric equivalent of radiance (lm·sr$^{-1}$·m$^{-2}$).

The term "photometry" refers to measurement of light, in terms of its perceived brightness to the human eye.

The term "brightness" refers to the subjective perception elicited by the luminance of a source.

The term "standard regimen" refers to the industry standard.

The term "about" as used in reference to a number refers to a range spanning from 10% below the number to 10% above the number. The term "about" as used herein in reference to a range refers to 10% below the lowest value of the listed range up to 10% above the highest value of the listed range.

The term "about" as used herein in reference to wavelength refers to 1% below the number to 1% above the number.

Throughout the specification herein, the application of this definition of "about" is optional, such that 'about a number' is understood to refer to +/−10% of that number, and alternately is understood to mean exactly that number or that number plus a range of a single unit or other approximations of the number.

NUMBERED EMBODIMENTS

Numbered embodiment 1 comprises a method of treating a plant seedling to improve long term hardiness and/or improve crop yield and/or quality characterized by the step of exposing the plant seedling, prior to a subsequent growth phase, with ultraviolet (UV) irradiation with at least one wavelength, only between 280-310 nm. Numbered embodiment 2 comprises the method of numbered embodiment 1, wherein the treatment of the plant seedling with UV irradiation is performed indoors. Numbered embodiment 3 comprises the method of numbered embodiments 1-2, further comprises exposing the plant seedling to UV light in the range of 2-15 days. Numbered embodiment 4 comprises the method of numbered embodiments 1-3, further comprises exposing the plant seedling to cyclic exposure of UV light. Numbered embodiment 5 comprises the method of numbered embodiments 1-4, further comprises maintaining the temperature at approximately between 12° C. to 35° C. during the treatment. Numbered embodiment 6 comprises the method of numbered embodiments 1-5, further comprises exposure to UV wavelength within the range 280-305 nm. Numbered embodiment 7 comprises the method of numbered embodiments 1-6, further comprises exposure to peak UV wavelength within the range 280-290 nm. Numbered embodiment 8 comprises the method of numbered embodiments 1-7, wherein the plant seedling is a fruit and vegetable species. Numbered embodiment 9 comprises the method of numbered embodiments 1-8, wherein the plant seedling is selected from the group including green lettuce, red lettuce, tomato, cucumber, broccoli, herb crops and eggplant. Numbered embodiment 10 comprises a device to administer ultraviolet (UV) irradiation to a plant seedling, characterized in that the device is configured to administer ultraviolet (UV) irradiation with at least one wavelength within the range 280-310 nm. Numbered embodiment 11 comprises the device of numbered embodiments 1-10, wherein the device includes a moving conveyor which alters the relative positions of at least one light emitter and the target area during the treatment. Numbered embodiment 12 comprises the device of numbered embodiments 1-11, wherein the light emitter is at least one light emitting diode (LED). Numbered embodiment 13 comprises the device of numbered embodiments 1-12, wherein the device is configured to also administer at least one wavelength in the visible spectrum between 400 to 800 nm. Numbered embodiment 14 comprises the device of numbered embodiments 1-13, wherein the device is configured to administer at least one a wavelength in the blue visible spectrum between 400 to 500 nm. Numbered embodiment 15 comprises the device of numbered embodiments 1-14, wherein the device is configured to administer at least one a wavelength in the red visible spectrum between 655-680 nm. Numbered embodiment 16 comprises a method of improving long term hardiness and/or crop yield and/or crop quality characterized by the steps of (a) exposing a plant seedling or seedlings, prior a subsequent growth phase, with ultraviolet (UV) light with at least one wavelength, only within the range 280-310 nm; and (b) selecting a plant seedling or seedlings for a subsequent growth phase. Numbered embodiment 17 comprises the method of numbered embodiments 1-16, wherein step (b) includes predicting or assessing hardiness of the plant seedling and/or resulting crop yield or crop quality of the plant seedling(s) or plant in order to select for seedling(s) or related seedling(s) undergoing similar UV treatment which show promising beneficial traits. Numbered embodiment 19 comprises a plant seedling, plant or harvestable crop following treatment according to any one of numbered embodiments 1-18. Numbered embodiment 20 comprises a method for improving hardiness and plant yield, comprising administering light enriched for UV wavelengths from 280 nm to 290 nm to a plant material. Numbered embodiment 21 comprises the method of numbered embodiments 1-20, wherein the plant material comprises material of a plant in family Rosaceae. Numbered embodiment 22 comprises the method of numbered embodiments 1-21, wherein the Rosaceae material is of a plant in genus a *Fragaria*. Numbered embodiment 23 comprises the method of numbered embodiments 1-22, wherein the plant material is a runner. Numbered embodiment 24 comprises the method of numbered embodiments 1-23, wherein the plant material is a seed. Numbered embodiment 25 comprises the method of numbered embodiments 1-24, wherein the plant material is a seedling. Numbered embodiment 26 comprises the method of numbered embodiments 1-25, wherein the plant material is a plant. Numbered embodiment 27 comprises the method of numbered embodiments 1-26, wherein the light is enriched for a UV wavelength of 280 nm. Numbered embodiment 28 comprises the method of numbered embodiments 1-27, wherein the light is enriched for a UV wavelength of 290 nm. Numbered embodiment 29 comprises the method of numbered embodiments 1-28, wherein the light comprises blue light. Numbered embodiment 30 comprises the method of numbered embodiments 1-29, wherein the light comprises red light. Numbered embodiment 31 comprises the method of numbered embodiments 1-30, wherein the light is administered for at least 1 day. Numbered embodiment 32 comprises the method of numbered embodiments 1-31, wherein the light is administered for at least 14 days. Numbered embodiment 33 comprises the method of numbered embodiments 1-32, wherein the light is administered for about 14 days. Numbered embodiment 34 comprises the method of numbered embodiments 1-33, wherein the yield is selected from a group consisting of an improved fruit fresh weight, improved number of fruit harvested, improved Brix content, improved fruit width, improved fruit length, improved leaf size, an improved leaf surface area, an improved dry weight, an improved nitrogen content, an improved shoot dry weight, an improved shoot fresh weight, an improved root dry weight, an improved vegetable development, an improved yield of fruiting parts, an increased weight of fruiting parts, improved hardiness, and an increased seed germination rate. Numbered embodiment 35 comprises the method of numbered embodiments 1-34, wherein the yield is improved by at least 5% compared to a plant from a non-UV-B irradiated seed. Numbered embodiment 36 comprises the method of numbered embodiments 1-35, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 37 comprises a method of growing a crop by reducing pesticide use without impacting loss due to pest damage comprising the steps of: (a) administering light enriched for at least one UV wavelength in a range from 280 nm to 290 nm to a plant material; (b) providing no more than 95% of the standard pesticide regimen; and (c) harvesting the crop, wherein the crop provides a greater yield than a comparable crop provided with the standard pesticide regimen but not supplemented with UV light. Numbered embodiment 38 comprises a method for improving hardiness and plant yield in a crop, comprising (a) administering light enriched for at least one UV wavelength in a range from 280 nm to 290 nm to a plant material; (b) providing a pesticide regimen, wherein the pesticide regimen is no more than 50% of the standard pesticide regimen; (c) harvesting the crop, and (d) measuring the plant yield, wherein the crop provides a greater yield than a comparable crop provided with the standard pesticide regimen but not supplemented with UV light. Numbered embodiment 39 comprises the method of numbered embodiments 1-38, wherein the plant material comprises plant material from a plant in family Rosaceae. Numbered embodiment 40 comprises the method of numbered embodiments 1-39, wherein the Rosaceae plant is of genus *Fragaria*. Numbered embodiment 41 comprises the method of numbered embodiments 1-40, wherein the plant material is a runner. Numbered embodiment 42 comprises the method of numbered embodiments 1-41, wherein the plant material is a seed. Numbered embodiment 43 comprises the method of numbered embodiments 1-42, wherein the plant material is a seedling. Numbered embodiment 44 comprises the method of numbered embodiments 1-43, wherein the plant material is a plant. Numbered embodiment 45 comprises the method of numbered embodiments 1-44, wherein the light is enriched for UV wavelength of 280 nm. Numbered embodiment 46 comprises the method of numbered embodiments 1-45, wherein the light is enriched for UV wavelength of 290 nm. Numbered embodiment 47 comprises the method of numbered embodiments 1-46, wherein the light comprises blue light. Numbered embodiment 48 comprises the method of numbered embodiments 1-47, wherein the light comprises red light. Numbered embodiment 49 comprises the method of numbered embodiments 1-48, wherein the light is administered for at least 1 day. Numbered embodiment 50 comprises the method of numbered embodiments 1-49, wherein the light is administered for at least 14 days. Numbered embodiment 51 comprises the method of numbered embodiments 1-50, wherein the light is administered for about 14 days. Numbered embodiment 52 comprises the method of numbered embodiments 1-51, wherein the yield is selected from a group consisting of an improved fruit fresh weight, improved number of fruit harvested, improved Brix content, improved fruit width, improved fruit length, improved leaf size, an improved leaf surface area, an improved dry weight, an improved nitrogen content, an improved shoot dry weight, an improved shoot fresh weight, an improved root dry weight, an improved vegetable development, an improved yield of fruiting parts, an increased weight of fruiting parts, improved hardiness, and an increased seed germination rate. Numbered embodiment 52 comprises the method of numbered embodiments 1-51, wherein the yield is improved by at least 5% compared to a plant from a non-UV-B irradiated seed. Numbered embodiment 53 comprises the method of numbered embodiments 1-52, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 54 comprises the method of numbered embodiments 1-53, wherein the pesticide regimen is no more than 60% of the standard pesticide regimen. Numbered embodiment 55 comprises the method of numbered embodiments 1-54, wherein the pesticide regimen is no more than 70% of the standard pesticide regimen. Numbered embodiment 56 comprises the method of numbered embodiments 1-55, wherein the pesticide regimen is no more than 80% of the standard pesticide regimen. Numbered embodiment 57 comprises a crop of any one of numbered embodiments 1-56. Numbered embodiment 58 comprises afield of any one of numbered embodiments 1-57. Numbered embodiment 59 comprises a method for improving yield of a fruiting component of a crop plant, comprising: administering light enriched for at least one UV wavelength in a range from 280 nm to 290 nm to a plant material at least 7 weeks before fruit is harvested. Numbered embodiment 60 comprises the method of numbered embodiments 1-59, wherein the light is enriched for UV wavelength of 280 nm. Numbered embodiment 61 comprises the method of numbered embodiments 1-60, wherein the light is enriched for UV wavelength of 290 nm. Numbered embodiment 62 comprises the method of numbered embodiments 1-61, wherein the light comprises blue light. Numbered embodiment 63 comprises the method of numbered embodiments 1-62, wherein the light comprises red light. Numbered embodiment 64 comprises the method of numbered embodiments 1-63, wherein the light is administered using a treatment regimen for a duration of at least 1 day. Numbered embodiment 65 comprises the method of numbered embodiments 1-64, wherein the light is administered using a treatment regimen for a duration of at least 14 days. Numbered embodiment 66 comprises the method of numbered embodiments 1-65, wherein the light is administered using a treatment regimen for a duration of about 14 days. Numbered embodiment 67 comprises the method of numbered embodiments 1-66, wherein the light is administered for about 10 hours total per day. Numbered embodiment 68 comprises the method of numbered embodiments 1-67, wherein the plant material is from a plant in family Rosaceae. Numbered embodiment 69 comprises the method of numbered embodiments 1-68, wherein the Rosaceae plant is of genus *Fragaria*. Numbered embodiment 70 comprises the method of numbered embodiments 1-69, wherein the plant material is from a fruiting plant. Numbered embodiment 71 comprises the method of numbered embodiments 1-70, wherein the plant material is from at least one of tomato, strawberry, and *cannabis*. Numbered embodiment 72 comprises the method of numbered embodiments 1-71, wherein the plant material is a runner. Numbered embodiment 73 comprises the method of numbered embodiments 1-72, wherein the plant material is a seed. Numbered embodiment 74 comprises the method of numbered embodiments 1-73, wherein the plant material is a seedling. Numbered embodiment 75 comprises the method of numbered embodiments 1-74, wherein the plant material is a plant. Numbered embodiment 76 comprises the method of numbered embodiments 1-75, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Numbered embodiment 77 comprises the method of numbered embodiments 1-76, wherein the improved yield is fruit fresh weight. Numbered embodiment 78 comprises the method of numbered embodiments 1-77, wherein the fruit fresh weight is improved by at least 5% compared to a non-UV-B irradiated plant material. Numbered embodiment 79 comprises the method of numbered embodiments 1-78, wherein the improved yield is number of fruit harvested. Numbered embodiment 80 comprises the method of numbered embodiments 1-79, wherein the number of fruit harvested is improved by at least 10% compared to a non-UV-B irradiated plant material. Numbered embodiment 81 comprises the method of numbered embodiments 1-80, wherein the improved yield is increased flowering parts. Numbered embodiment 82 comprises the method of numbered embodiments 1-81, wherein the improved yield is improved Brix content. Numbered embodiment 83 comprises the method of numbered embodiments 1-82, wherein the yield is improved by at least 5% compared to a non-UV-B irradiated plant material. Numbered embodiment 84 comprises a method for improving yield of a fruiting component of a crop plant, comprising: administering light enriched for at least one UV wavelength in a range from 280 nm to 290 nm to a plant material during a propagation stage of the plant material.

Numbered embodiment 85 comprises the method of numbered embodiments 1-84, wherein the light is enriched for UV wavelength of 280 nm. Numbered embodiment 86 comprises the method of numbered embodiments 1-85, wherein the light is enriched for UV wavelength of 290 nm. Numbered embodiment 87 comprises the method of numbered embodiments 1-86, wherein the light comprises blue light. Numbered embodiment 88 comprises the method of numbered embodiments 1-87, wherein the light comprises red light. Numbered embodiment 89 comprises the method of numbered embodiments 1-88, wherein the light is administered using a treatment regimen for a duration of at least 1 day. Numbered embodiment 90 comprises the method of numbered embodiments 1-89, wherein the light is administered using a treatment regimen for a duration of at least 14 days. Numbered embodiment 91 comprises the method of numbered embodiments 1-90, wherein the light is administered using a treatment regimen for a duration of about 14 days. Numbered embodiment 92 comprises the method of numbered embodiments 1-91, wherein the light is administered for about 10 hours total per day. Numbered embodiment 93 comprises the method of numbered embodiments 1-92, wherein the plant material is from a plant in family Rosaceae. Numbered embodiment 94 comprises the method of numbered embodiments 1-93, wherein the Rosaceae plant is of genus *Fragaria*. Numbered embodiment 95 comprises the method of numbered embodiments 1-94, wherein the plant material is from a fruiting plant. Numbered embodiment 96 comprises the method of numbered embodiments 1-95, wherein the plant material is from at least one of tomato, strawberry, and *cannabis*. Numbered embodiment 97 comprises the method of numbered embodiments 1-96, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Numbered embodiment 98 comprises the method of numbered embodiments 1-97, wherein the improved yield is fruit fresh weight. Numbered embodiment 99 comprises the method of numbered embodiments 1-98, wherein the fruit fresh weight is improved by at least 5% compared to a non-UV-B irradiated plant material. Numbered embodiment 100 comprises the method of numbered embodiments 1-99, wherein the improved yield is number of fruit harvested. Numbered embodiment 101 comprises the method of numbered embodiments 1-100, wherein the number of fruit harvested is improved by at least 10% compared to a non-UV-B irradiated plant material. Numbered embodiment 102 comprises the method of numbered embodiments 1-101, wherein the improved yield is increased flowering parts. Numbered embodiment 103 comprises the method of numbered embodiments 1-102, wherein the improved yield is improved Brix content. Numbered embodiment 104 comprises the method of numbered embodiments 1-103, wherein the improved yield is improved by at least 5% compared to a non-UV-B irradiated plant material. Numbered embodiment 105 comprises the method of numbered embodiments 1-104, wherein the improved yield occurs at least 1 week following administration of the light. Numbered embodiment 106 comprises the method of numbered embodiments 1-105, wherein the improved yield occurs 1 week, 2 weeks, 3 weeks, 4 weeks, 5 weeks, 6 weeks, 7 weeks, or 8 weeks following administration of the light. Numbered embodiment 107 comprises the method of numbered embodiments 1-106, wherein the propagation stage comprises runners. Numbered embodiment 108 comprises the method of numbered embodiments 1-107, wherein the propagation stage comprises shoots. Numbered embodiment 109 comprises the method of numbered embodiments 1-108, wherein the propagation stage comprises cuttings. Numbered embodiment 110 comprises a method for improving yield of a fruiting component of a crop plant, comprising: (a) administering light enriched for at least one UV wavelength in a range from 280 nm to 290 nm to a plant material; and (b) collecting an increased number of fruit than expected number of fruit for an untreated field. Numbered embodiment 111 comprises the method of numbered embodiments 1-110, wherein the light is enriched for UV wavelength of 280 nm. Numbered embodiment 112 comprises the method of numbered embodiments 1-111, wherein the light is enriched for UV wavelength of 290 nm. Numbered embodiment 113 comprises the method of numbered embodiments 1-112, wherein the light comprises blue light. Numbered embodiment 114 comprises the method of numbered embodiments 1-113, wherein the light comprises red light. Numbered embodiment 115 comprises the method of numbered embodiments 1-114, wherein the light is administered using a treatment regimen for a duration of at least 1 day. Numbered embodiment 116 comprises the method of numbered embodiments 1-115, wherein the light is administered using a treatment regimen for a duration of at least 14 days. Numbered embodiment 117 comprises the method of numbered embodiments 1-116, wherein the light is administered using a treatment regimen for a duration of about 14 days. Numbered embodiment 118 comprises the method of numbered embodiments 1-117, wherein the light is administered for about 10 hours total per day. Numbered embodiment 119 comprises the method of numbered embodiments 1-118, wherein the plant material is from a plant in family Rosaceae. Numbered embodiment 120 comprises the method of numbered embodiments 1-119, wherein the Rosaceae plant is of genus *Fragaria*. Numbered embodiment 121 comprises the method of numbered embodiments 1-120, wherein the plant material is from a fruiting plant. Numbered embodiment 122 comprises the method of numbered embodiments 1-121, wherein the plant material is from at least one of tomato, strawberry, and *cannabis*. Numbered embodiment 123 comprises the method of numbered embodiments 1-122, wherein the increased number of fruit is increased by at least 5%. Numbered embodiment 124 comprises the method of numbered embodiments 1-123, wherein the expected number of fruit for the untreated field is determined by a national average. Numbered embodiment 125 comprises the method of numbered embodiments 1-124, wherein the expected number of fruit for the untreated field is determined by a historical average for a growing region. Numbered embodiment 126 comprises the method of numbered embodiments 1-125, wherein the untreated field comprises an adjacent field. Numbered embodiment 127 comprises the method of numbered embodiments 1-126, wherein the untreated field comprises a field of about the same size. Numbered embodiment 128 comprises a method for improving yield of a fruiting component of a crop plant, comprising: administering light enriched for at least one UV wavelength in a range from 280 nm to 290 nm to a plant material, wherein the yield is improved by at least 5%. Numbered embodiment 129 comprises the method of numbered embodiments 1-128, wherein the light is enriched for UV wavelength of 280 nm. Numbered embodiment 130 comprises the method of numbered embodiments 1-129, wherein the light is enriched for UV wavelength of 290 nm. Numbered embodiment 131 comprises the method of numbered embodiments 1-130, wherein the light comprises blue light. Numbered embodiment 132 comprises the method of numbered embodiments 1-131, wherein the light comprises red light. Numbered embodiment 133 comprises the method of numbered embodiments 1-132, wherein the light is administered using a treatment regimen for a duration of at least 1 day. Numbered embodiment 134 comprises the method of numbered embodiments 1-133, wherein the light is administered using a treatment regimen for a duration of at least 14 days. Numbered embodiment 135 comprises the method of numbered embodiments 1-134, wherein the light is administered using a treatment regimen for a duration of about 14 days. Numbered embodiment 136 comprises the method of numbered embodiments 1-135, wherein the light is administered for about 10 hours total per day. Numbered embodiment 137 comprises the method of numbered embodiments 1-136, wherein the plant material is from a plant in family Rosaceae. Numbered embodiment 138 comprises the method of numbered embodiments 1-137, wherein the Rosaceae plant is of genus *Fragaria*. Numbered embodiment 139 comprises the method of numbered embodiments 1-138, wherein the plant material is from a fruiting plant. Numbered embodiment 140 comprises the method of numbered embodiments 1-139, wherein the plant material is from at least one of tomato, strawberry, and *cannabis*. Numbered embodiment 141 comprises the method of numbered embodiments 1-140, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Numbered embodiment 142 comprises the method of numbered embodiments 1-141, wherein the improved yield is fruit fresh weight. Numbered embodiment 143 comprises the method of numbered embodiments 1-142, wherein the improved yield is number of fruit harvested. Numbered embodiment 144 comprises the method of numbered embodiments 1-143, wherein the improved yield is increased flowering parts. Numbered embodiment 145 comprises the method of numbered embodiments 1-144, wherein the improved yield is improved Brix content. Numbered embodiment 146 comprises the method of numbered embodiments 1-145, wherein the improved yield is compared to a non-UV-B irradiated plant material. Numbered embodiment 147 comprises a field having at least 10% improved yield of fruiting components of a crop plant following administration of light enriched for UV-B in a range of 280 nm to 290 nm compared to a field not administered UV-B. Numbered embodiment 148 comprises a field having more than about 50000 pounds of fruiting components of a crop plant per acre following administration of light enriched for UV-B in a range of 280 nm to 290 nm compared to a field not administered UV-B. Numbered embodiment 149 comprises the field of numbered embodiments 1-148, wherein no more than 95% of at least one of a standard fertilizer regimen, standard pesticide regimen, standard herbicide regimen, standard insecticide regimen, and standard water regimen is administered. Numbered embodiment 150 comprises the field of numbered embodiments 1-149, wherein no more than 80% of at least one of a standard fertilizer regimen, standard pesticide regimen, standard herbicide regimen, standard insecticide regimen, and standard water regimen is administered. Numbered embodiment 151 comprises the field of numbered embodiments 1-150, wherein no more than 70% of at least one of a standard fertilizer regimen, standard pesticide regimen, standard herbicide regimen, standard insecticide regimen, and standard water regimen is administered. Numbered embodiment 152 comprises the field of numbered embodiments 1-151, wherein no more than 60% of at least one of a standard fertilizer regimen, standard pesticide regimen, standard herbicide regimen, standard insecticide regimen, and standard water regimen is administered. Numbered embodiment 153 comprises the field of numbered embodiments 1-152, wherein the light is enriched for UV wavelength of 280 nm. Numbered embodiment 154 comprises the field of numbered embodiments 1-153, wherein the light is enriched for UV wavelength of 290 nm. Numbered embodiment 155 comprises the field of numbered embodiments 1-154, wherein the light comprises blue light. Numbered embodiment 156 comprises the field of numbered embodiments 1-155, wherein the light comprises red light. Numbered embodiment 157 comprises the field of numbered embodiments 1-156, wherein the light is administered using a treatment regimen for a duration of at least 1 day. Numbered embodiment 158 comprises the field of numbered embodiments 1-157, wherein the light is administered using a treatment regimen for a duration of at least 14 days. Numbered embodiment 159 comprises the field of numbered embodiments 1-158, wherein the light is administered using a treatment regimen for a duration of about 14 days. Numbered embodiment 160 comprises the field of numbered embodiments 1-159, wherein the light is administered for about 10 hours total per day. Numbered embodiment 161 comprises the field of numbered embodiments 1-160, wherein the crop plant is from a plant in family Rosaceae. Numbered embodiment 162 comprises the field of numbered embodiments 1-161, wherein the Rosaceae plant is of genus *Fragaria*. Numbered embodiment 163 comprises the field of numbered embodiments 1-162, wherein the crop plant is from at least one of tomato, strawberry, and *cannabis*. Numbered embodiment 164 comprises the field of numbered embodiments 1-163, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Numbered embodiment 165 comprises the field of numbered embodiments 1-164, wherein the improved yield is fruit fresh weight. Numbered embodiment 166 comprises the field of numbered embodiments 1-165, wherein the improved yield is number of fruit harvested. Numbered embodiment 167 comprises the field of numbered embodiments 1-166, wherein the improved yield is increased flowering parts. Numbered embodiment 168 comprises the field of numbered embodiments 1-167, wherein the improved yield is improved Brix content. Numbered embodiment 169 comprises a method for improving yield of a fruiting component of a crop plant, comprising: subjecting a plant material to a treatment regimen comprising light enriched for at least one UV wavelength in a range from 280 nm to 295 nm and at least one of a treatment distance from the plant material and a light source in a range of about 30 mm to about 120 mm, a speed of a moving light source in a range of about 40 to about 60 mm per second, a light source timing cycle in a range of about 90 to about 280 seconds, a number of cycles per day in a range of about 380 to about 500 cycles per day, an irradiance of the UV wavelength in a range of about 15 to about 40 umol cm$^{-2}$ s$^{-1}$, a wavelength of blue light in a range of about 440 nm to about 460 nm, an irradiance of blue light in a range of about 30 to about 150 umol m$^{-2}$ s$^{-1}$, a wavelength of red light in a range of about 640 nm to about 680 nm, an irradiance of red light in a range of about 60 to about 300 umol m$^{-2}$ s$^{-1}$, and a number of days of the treatment regimen in a range of about 5 to about 20 days. Numbered embodiment 170 comprises the method of numbered embodiments 1-169, wherein the at least one UV wavelength is peaking at 282 nm. Numbered embodiment 171 comprises the method of numbered embodiments 1-170, wherein the at least one UV wavelength is peaking at 285 nm. Numbered embodiment 172 comprises the method of numbered embodiments 1-171, wherein the at least one UV wavelength is peaking at 287 nm. Numbered embodiment 173 comprises the method of numbered embodiments 1-172, wherein the at least one UV wavelength is peaking at 291 nm. Numbered embodiment 174 comprises the method of numbered embodiments 1-173, wherein the at least one UV wavelength is peaking at 292 nm. Numbered embodiment 175 comprises the method of numbered embodiments 1-174, wherein the plant material is from at least one of tomato, strawberry, and *cannabis*. Numbered embodiment 176 comprises the method of numbered embodiments 1-175, wherein the plant material is a runner. Numbered embodiment 177 comprises the method of numbered embodiments 1-176, wherein the plant material is a seed. Numbered embodiment 178 comprises the method of numbered embodiments 1-177, wherein the plant material is a seedling. Numbered embodiment 179 comprises the method of numbered embodiments 1-178, wherein the plant material is a plant. Numbered embodiment 180 comprises the method of numbered embodiments 1-179, wherein the crop plant is from a plant in family Rosaceae. Numbered embodiment 181 comprises the method of numbered embodiments 1-180, wherein the Rosaceae plant is of genus *Fragaria*. Numbered embodiment 182 comprises the method of numbered embodiments 1-181, wherein the crop plant is from at least one of tomato, strawberry, and *cannabis*. Numbered embodiment 183 comprises the method of numbered embodiments 1-182, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Numbered embodiment 184 comprises the method of numbered embodiments 1-183, wherein the improved yield is fruit fresh weight. Numbered embodiment 185 comprises the method of numbered embodiments 1-184, wherein the improved yield is number of fruit harvested. Numbered embodiment 186 comprises the method of numbered embodiments 1-185, wherein the improved yield is increased flowering parts. Numbered embodiment 187 comprises the method of numbered embodiments 1-186, wherein the improved yield is improved Brix content. Numbered embodiment 188 comprises the method of numbered embodiments 1-187, wherein the improved yield is improved by at least 5%. Numbered embodiment 189 comprises a device configured to administer a treatment regimen comprising light enriched for at least one UV wavelength in a range from 280 nm to 295 nm to a plant material and to control at least one of a treatment distance from the plant material and a light source in a range of about 30 mm to about 120 mm, a speed of a moving light source in a range of about 40 to about 60 mm per second, a light source timing cycle in a range of about 90 to about 280 seconds, a number of cycles per day in a range of about 380 to about 500 cycles per day, an irradiance of the UV wavelength in a range of about 15 to about 40 umol cm$^{-2}$ s$^{-1}$, a wavelength of blue light in a range of about 440 nm to about 460 nm, an irradiance of blue light in a range of about 30 to about 150 umol m$^{-2}$ s$^{-1}$, a wavelength of red light in a range of about 640 nm to about 680 nm, an irradiance of red light in a range of about 60 to about 300 umol s$^{-1}$, and a number of days of the treatment regimen in a range of about 5 to about 20 days. Numbered embodiment 190 comprises the device of numbered embodiments 1-189, wherein the at least one UV wavelength is peaking at 282 nm. Numbered embodiment 191 comprises the device of numbered embodiments 1-190, wherein the at least one UV wavelength is peaking at 285 nm. Numbered embodiment 192 comprises the device of numbered embodiments 1-191, wherein the at least one UV wavelength is peaking at 287 nm. Numbered embodiment 193 comprises the device of numbered embodiments 1-192, wherein the at least one UV wavelength is peaking at 291 nm. Numbered embodiment 194 comprises the device of numbered embodiments 1-193, wherein the at least one UV wavelength is peaking at 292 nm. Numbered embodiment 195 comprises the device of numbered embodiments 1-194, wherein the plant material is from at least one of tomato, strawberry, and *cannabis*. Numbered embodiment 196 comprises the device of numbered embodiments 1-195, wherein the plant material is a runner. Numbered embodiment 197 comprises the device of numbered embodiments 1-196, wherein the plant material is a seed. Numbered embodiment 198 comprises the device of numbered embodiments 1-197, wherein the plant material is a seedling. Numbered embodiment 199 comprises the device of numbered embodiments 1-198, wherein the plant material is a plant. Numbered embodiment 200 comprises the device of numbered embodiments 1-199, wherein the crop plant is from a plant in family Rosaceae. Numbered embodiment 201 comprises the device of numbered embodiments 1-200, wherein the Rosaceae plant is of genus *Fragaria*. Numbered embodiment 202 comprises the device of numbered embodiments 1-201, wherein the crop plant is from at least one of tomato, strawberry, and *cannabis*. Numbered embodiment 203 comprises the device of numbered embodiments 1-202, wherein the improved yield is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, weight of fruiting parts, hardiness, and seed germination rate. Numbered embodiment 204 comprises the device of numbered embodiments 1-203, wherein the improved yield is fruit fresh weight. Numbered embodiment 205 comprises the device of numbered embodiments 1-204, wherein the improved yield is number of fruit harvested. Numbered embodiment 206 comprises the device of numbered embodiments 1-205, wherein the improved yield is increased flowering parts. Numbered embodiment 207 comprises the device of numbered embodiments 1-206, wherein the improved yield is improved Brix content. Numbered embodiment 208 comprises the device of numbered embodiments 1-207, wherein the improved yield is improved by at least 5%.

Examples

Example 1—Example Use of UV Light to Increase Hardiness and/or Crop Yield

Green lettuce plants were germinated in vermiculite, and upon appearance of cotyledons were transferred into a standard potting mixture. Plants were maintained under a visible light intensity of 400 µmol m$^{-2}$ s$^{-1}$ for 10 days, at a photoperiod of 14 hr/10 hr light/dark. Plants were then exposed to a narrow-band UV dosage peaking at 290 nm using an LED (Light Emitting Diode) array. At the same time, a proportion of the same population of lettuce plants were exposed to a narrow-band UV dosage peaking at 354 nm using an LED (Light Emitting Diode) array.

The plants were exposed to a UV dosage for seven days at the same time as being exposed to background visible light. At the end of the seven days of UV treatment, plants were planted into a rotivated soil bed at an adjacent outdoor field site, with a selection of those plants destructively harvested for assessment of the three measured variables of average Hardiness Index (H).

The plants then remained in the field site, enduring field weather conditions for a period of 11 weeks. Six replicate plants were assessed at the end of the 11 weeks of field growth for whole shoot fresh weight, i.e. stem and leaves combined. Whole shoot fresh weight is a key indicator of final harvest yield size for many crop plants.

The results are shown in Table 1 below. It is evident that the sample treated with UV light at 290 nm according to the present disclosure shows a dramatic increase in total shoot fresh weight at 11 weeks in the field, compared to the sample treated with UV light at 354 nm (outside the UV-B spectrum).

Comparatively, the H value, determined using the hardiness index according to the present disclosure, at the end of the 7 day UV treatment phase, is shown to provide a useful prediction and/or selection method for long term plant hardiness and crop yield and/or quality. In this example, the H value is 3.04 for the sample treated at 290 nm according to the present disclosure, compared to an H value of 2.96 for the sample treated at 354 nm. The difference of 0.08 between the two samples corresponds to a prediction of almost 10% increase in hardiness. This prediction corresponds well with the preliminary results seen in the field at 11 weeks post-transfer from the greenhouse.

Although only lettuce was tested in the preliminary study, it is expected that many other crops and/or other plants will display the same beneficial results seen. Ongoing trials are being performed in various vegetable crops and herbs to further exemplify the disclosure across different species.

TABLE 1

Plant hardiness response (mean of 6 plants ± 1 standard error)

| Hardiness index value (H) | Light treatment | Plant total shoot fresh weight (g) |
|---|---|---|
| 3.04 | 290 nm | 27.74* ± 4.0 |
| 2.96 | 354 nm | 16.65 ± 4.5 |

*indicates significant increase compared to 354 nm treatment according to t-test (P < 0.05)

Example 2—Green Lettuce Disease and Field Assessed Fresh Weights

Green lettuce seedlings grown as described above, were planted 24 hrs after UV treatment (according to the present disclosure), into a lettuce field planting site carrying Sclerotina fungal disease. A moving light array treatment method was used according to New Zealand Patent Application Number 621039. The UV dosage regime included treatment for 7 days (12 hours on/12 hours off) in 2 week old plants using 0.16798 W m$^{-2}$ s$^{-1}$ [at a peak wavelength of 303 nm].

An assessment was carried out to determine the "hardiness" of the plants of the UV treated seedlings according to the present disclosure compared to untreated seedlings, 24 hrs after UV treatment had finished. The results in Table 2 show that leaf area (or 'SLA' as a component of Hardiness Index) was reduced in treated seedlings immediately following UV treatment, which is a indication that increased hardiness had been achieved.

TABLE 2

| Leaf area (cm$^2$) | UV | S.E. |
|---|---|---|
| UV | 11.07* | 0.40 |
| No UV | 13.38 | 0.36 |

*indicates significant decrease compared to No UV treatment according to t-test (P < 0.05)

Disease incidence and fresh weight was then assessed in all plants at 5 weeks post treatment. Results are shown in Table 3 and Table 3A below.

The results show that the UV treated lettuce seedlings showed increased fresh weight, and also a greater resistance to the fungus, assessed by a rating scale, describing the number of plants that were displaying a particular severity of disease infection.

TABLE 3

| Fresh weight (g) | UV | S.E. | No UV | S.E. |
|---|---|---|---|---|
| Whole lettuce plant | 833.63* | 44.79 | 642.84 | 56.20 |
| Trimmed lettuce head | 672.42 | 41.07 | 577.32 | 41.92 |

*indicates significant decrease compared to No UV treatment according to t-test (P < 0.05)

TABLE 3A

| | Number of plants | |
|---|---|---|
| Infection type | UV | No UV |
| No Infection | 9 | 3 |
| First signs of infection | 3 | 2 |
| Infected | 3 | 4 |
| Severely Infected | 1 | 7 |

Example 3—Red Lettuce Hardiness and Crop Yield Assessment

A trial was performed on red lettuce seedlings, grown and then field-planted after UV treatment as described above, to determine the effect of UV treatment as claimed compared to control groups. A moving light array treatment method was used according to New Zealand Patent Application Number 621039. The UV dosage regime included treatment for 7 days (12 hours on/12 hours off) at age 2 weeks using 0.06374 W m$^{-2}$ s$^{-1}$ [at a peak wavelength of 286 nm].

The results are shown below in Table 4. Following an outside standing period of 9 days, a H value of 3.08 was measured in UV-treated plants. In addition, the UV-treated samples showed clear improvements in fresh weight and leaf area compared to the No UV controls at 9 days post treatment, and at final harvest at 5 weeks post-field planting.

TABLE 4

| Variable | UV | S.E. | No UV | S.E. |
|---|---|---|---|---|
| Post-UV treatment harvest [7 days] | | | | |
| Fresh Weight (g) | 0.62 | 0.05 | 0.71 | 0.07 |
| Leaf Area (cm$^2$) | 23.10 | 1.73 | 25.49 | 2.22 |
| Dry Weight (g) | 0.03 | 0.00 | 0.04 | 0.00 |
| Specific Leaf Weight | 0.00138 | 0.00005 | 0.00147 | 0.00005 |
| Harvest following outside standing period of 9 days | | | | |
| Fresh Weight (g) | 1.57 | 0.09 | 1.38 | 0.12 |
| Leaf Area (cm$^2$) | 46.43 | 2.26 | 42.95 | 3.31 |
| Dry Weight (g) | 0.11 | 0.01 | 0.10 | 0.01 |
| Specific Leaf Weight | 0.0023 | 0.0001 | 0.0023 | 0.0001 |
| Final harvest following field planting period of 5 weeks | | | | |
| Fresh Weight (g) | 7.35 | 1.04 | 6.54 | 0.82 |
| Leaf Area (cm$^2$) | 146.49 | 19.98 | 124.68 | 12.73 |

Example 4—Cucumber Hardiness and Crop Yield Assessment

A trial was performed on cucumber seedlings (using growing conditions as described above) to determine the effect of UV treatment as claimed compared to control groups. A moving light array treatment method was used according to New Zealand Patent Application Number 621039. The UV dosage regime included treatment for 7 days (12 hours on/12 hours off) at age 2 weeks using 0.06374 W m$^2$ s$^{-1}$ [at a peak wavelength of 286 nm].

The results are shown below in Table 5. The UV-treated samples showed lower fresh weight at 7 days post treatment (during an outside growing period) than the No UV treated samples. Yet, by day 12, the UV treated sample displayed fresh weight values that were higher than those observed in the No UV treated sample. The leaf area of plants also increased more in the UV treated sample between day 7 and 12 in the UV treated sample compared to the untreated sample. This example illustrates the 'springboard' effect of the UV treatment method regarding plant productivity in the days (or weeks) following treatment.

TABLE 5

| Variable | UV | S.E. | No UV | S.E. |
|---|---|---|---|---|
| Post-UV treatment harvest [7 days] | | | | |
| Fresh Weight (g) | 2.44 | 0.06 | 2.55 | 0.13 |
| Leaf Area (cm$^2$) | 56.89 | 1.19 | 53.04 | 3.51 |
| Dry Weight (g) | 0.21 | 0.01 | 0.19 | 0.02 |
| Specific Leaf Weight | 0.0036 | 0.0002 | 0.0039 | 0.0003 |
| Final harvest following outside standing period of 12 days | | | | |
| Fresh Weight (g) | 3.11 | 0.25 | 2.85 | 0.11 |
| Leaf Area (cm$^2$) | 63.86 | 6.70 | 56.56 | 3.22 |
| Dry Weight (g) | 0.25 | 0.02 | 0.23 | 0.01 |
| Specific Leaf Weight | 0.0040 | 0.0002 | 0.0042 | 0.0002 |

A further test was performed to assess cold tolerance in cucumber. The results are shown below in Table 6. The results show that the UV treatment according to the present disclosure led to an improved hardiness in the cucumber plants.

TABLE 6

| Cold stress plant damage scoring following outside standing period of 12 days | | | | | |
|---|---|---|---|---|---|
| | Nil (0) | Low (1) | Med (2) | High (3) | Total infection ((1) + (2) + (3)) |
| UV | 65% | 18% | 12% | 4% | 35% |
| No UV | 14% | 37% | 31% | 18% | 86% |

Total of 49 plants per treatment assessed: % are number of plants with a particular stress score by 12 days

Example 5—Tomato Hardiness and Crop Yield Assessment

A trial was performed on tomato seedlings (grown as described above) to determine the effect of UV treatment as claimed compared to control plants. A moving light array treatment method was used according to New Zealand Patent Application Number 621039. The UV dosage regime included treatment for 7 days (12 hours on/12 hours off) at age 3 weeks using 0.06374 W m$^{-2}$ s$^{-1}$ [at a peak wavelength of 286 nm].

The results are shown below in Table 7. When measured at 7 days, the UV-treated samples showed significant increases in fresh weight, leaf area and dry weight compared to the no-UV treatment samples. This equated to an overall H value of 3.55 at 7 days post UV-treatment. This is supportive that there will be an overall increased yield at harvest as a result of the UV treatment of the tomato seedlings. To illustrate this, a further harvest of plant biomass was taken after an outside standing period of 6 days. This harvest indicated that the described increases in plant growth continued beyond the completion of the UV treatment.

TABLE 7

| Variable | UV | S.E. | No UV | S.E. |
|---|---|---|---|---|
| Post-UV treatment harvest [7 days] | | | | |
| Fresh Weight (g) | 1.06 | 0.34 | 0.46 | 0.08 |
| Leaf Area (cm$^2$) | 30.09 | 8.94 | 12.03 | 1.42 |
| Dry Weight (g) | 0.12 | 0.03 | 0.06 | 0.02 |
| Specific Leaf Weight | 0.0041 | 0.0002 | 0.0049 | 0.0008 |
| Final harvest following outside standing period of 6 days | | | | |
| Fresh Weight (g) | 1.65 | 0.23 | 0.82 | 0.20 |
| Leaf Area (cm$^2$) | 38.47 | 5.01 | 18.12 | 2.83 |
| Dry Weight (g) | 0.19 | 0.03 | 0.10 | 0.02 |
| Specific Leaf Weight | 0.0047 | 0.0002 | 0.0058 | 0.0004 |

Example 6—Eggplant Hardiness and Crop Yield Assessment

A trial was performed on eggplant seedlings (grown as described above) to determine the effect of UV treatment as claimed compared to control groups. A moving light array treatment method was used according to New Zealand Patent Application Number 621039. The UV dosage regime included treatment for 7 days (12 hours on/12 hours off) at age 3 weeks using 0.06374 W m$^{-2}$ s$^{-1}$ [at a peak wavelength of 286 nm].

The results are shown below in Table 8. When measured at 7 days (immediately following UV treatment), the UV-treated samples showed similar or lower values in fresh weight, leaf area and dry weight compared to the no-UV treatment samples. Yet, by final harvest at 6 days, following an outside standing period of 6 days, fresh weight, leaf area, dry weight and specific leaf weight all had increased beyond the values seen in the No UV treatment samples. The beneficial results can therefore be observed from the Hardiness Index (or any one or number of variables relating to growth of the plant), showing an H value of 3.01 at the 7 day post-UV treatment harvest.

The data are supportive there will be an overall increased yield at harvest as a result of the UV treatment of the eggplant seedlings.

TABLE 8

| Variable | UV | S.E. | No UV | S.E |
|---|---|---|---|---|
| Post-UV treatment harvest [7 days] | | | | |
| Fresh Weight | 0.43 | 0.05 | 0.46 | 0.05 |
| Leaf Area | 13.72 | 1.52 | 14.45 | 1.32 |
| Dry Weight | 0.05 | 0.01 | 0.05 | 0.01 |
| Specific Leaf Weight | 0.0036 | 0.0004 | 0.0035 | 0.0004 |
| Final harvest following outside standing period of 6 days | | | | |
| Fresh Weight | 0.68 | 0.05 | 0.59 | 0.04 |
| Leaf Area | 17.94 | 1.32 | 17.55 | 1.44 |
| Dry Weight | 0.08 | 0.01 | 0.07 | 0.01 |
| Specific Leaf Weight | 0.0044 | 0.0001 | 0.0041 | 0.0001 |

Example 7—Assessing UV Spectrum for Beneficial Effects

An experiment was performed to assess the useful UV wavelength range for plant growth regulation (as a measure of hardiness) in green lettuce. This was measured by assessing shoot dry weight (as a component of the Hardiness index). Lettuce plants were grown as described above, and were exposed to a range of UV dosages (three doses for each wavelength) at selected wavelength peaks (which are listed in Table 9) using a series of LED (Light Emitting Diode) arrays for six days. Control plants which were not exposed to UV were used for comparison to UV treated plants. Whole shoot leaf dry weights were measured following the irradiation period. Shoot leaf dry weight measurements were expressed relative to untreated controls to deduce dosage responses per waveband. Following this, dose responses were developed based on dose range responses described above. The relative dose-based responses at the different wavelengths selected were then normalized to zero at 303 nm, and were interpolated to derive a description of the spectral response (or Quantum Effectiveness; in other words, an increased value indicates an increase in shoot dry weight for that given wavelength) for this aspect of hardiness. The results of this interpolation are in Table 10 and are plotted for ease of clarity in FIG. 1. It can be seen there is a sharp decline in improvements in this attribute of hardiness at a wavelengths below 290 nm, and the spectral response for this attribute of hardiness declines to <1.0 at 304 nm.

TABLE 9

| Wavelength (nm) | Relative quantum response | Normalized quantum effectiveness |
|---|---|---|
| 290 | 0.9588 | 184.38 |
| 303 | 0.0052 | 1.00 |
| 319 | −0.0127 | −2.44 |
| 336 | −0.0172 | −3.31 |

TABLE 9-continued

| Wavelength (nm) | Relative quantum response | Normalized quantum effectiveness |
|---|---|---|
| 354 | −0.0019 | −0.37 |

Table 10 shows a table of the interpolated quantum effectiveness for plant growth regulation of green lettuce. It should be appreciated that linear interpolation was used to interpolate quantum effectiveness values for this example, and that there are a variety of methods which may be used to interpolate between quantum effectiveness values.

TABLE 10

| Wavelength (nm) | Normalized quantum effectiveness |
|---|---|
| 290 | 184.38 |
| 291 | 170.28 |
| 292 | 156.17 |
| 293 | 142.07 |
| 294 | 127.96 |
| 295 | 113.85 |
| 296 | 99.75 |
| 297 | 85.64 |
| 298 | 71.53 |
| 299 | 57.43 |
| 300 | 43.32 |
| 301 | 29.21 |
| 302 | 15.11 |
| 303 | 1 |
| 304 | 0.923076923 |
| 305 | 0.846153846 |
| 306 | 0.769230769 |
| 307 | 0.692307692 |
| 308 | 0.615384615 |
| 309 | 0.538461538 |
| 310 | 0.461538462 |
| 311 | 0.384615385 |
| 312 | 0.307692308 |
| 313 | 0.230769231 |
| 314 | 0.153846154 |
| 315 | 0.076923077 |
| 316 | 0 |
| 317 | 0 |
| 318 | 0 |
| 319 | 0 |
| 320 | 0 |
| 321 | 0 |
| 322 | 0 |
| 323 | 0 |
| 324 | 0 |
| 325 | 0 |
| 326 | 0 |
| 327 | 0 |
| 328 | 0 |
| 329 | 0 |
| 330 | 0 |
| 331 | 0 |
| 332 | 0 |
| 333 | 0 |
| 334 | 0 |
| 335 | 0 |
| 336 | 0 |
| 337 | 0 |
| 338 | 0 |
| 339 | 0 |
| 340 | 0 |
| 341 | 0 |
| 342 | 0 |
| 343 | 0 |
| 344 | 0 |
| 345 | 0 |
| 346 | 0 |
| 347 | 0 |

TABLE 10-continued

| Wavelength (nm) | Normalized quantum effectiveness |
|---|---|
| 348 | 0 |
| 349 | 0 |
| 350 | 0 |
| 351 | 0 |
| 352 | 0 |
| 353 | 0 |
| 354 | 0 |

The shoot dry weight measurements were made at end of the 7 day irradiation treatment, and prior to the subsequent part of the plants' life in the outdoor environment. Wavelengths from 290-354 nm were used, and the preliminary results are shown in FIG. 1. In this preliminary study, a wavelength between 280-290 nm was not tested as the LEDs used had a lowest peak irradiation at 290 nm. However, it can be seen from the curve in FIG. 1 that an upwards trend towards 280 nm can be seen, and could be reasonably expected.

In a similar study (results shown in Table 11 below), it is shown that even minor fluctuations outside the claimed range of 280-310 nm UV-B wavelength can lead to substantial decrease in the Hardiness Index at the seedling stage (from 3.76 to 2.79), and losses and/or lack of improvement in plant leaf area at final harvest at 70 days (measured as % of non-treated control plants). Additionally, as per the interpolated example described above, seedling-stage plant dry weight was substantially improved within the desired treatment wavelength range.

TABLE 11

| | Seedling stage parameters [1 day after treatment] | | | | | Final harvest [70 days after treatment] |
|---|---|---|---|---|---|---|
| Wavelength (nm) | Shoot fresh weight (g) | Leaf area (cm²) | Specific leaf weight | Shoot dry weight | Hardiness Index at seedling stage | Plant leaf area in treated plants as % of non-treated control plants |
| 290 | 0.463 | 10.43 | 0.0053 | 0.055 | 3.76 | 106 |
| 319 | 0.375 | 10.52 | 0.0029 | 0.031 | 2.79 | 99 |

Example 8—UV-B Radiation on Strawberry Cultivars

Effects of UV-B treatment was assessed in strawberry plants. UV-B wavelengths of 280 nm or 290 nm were tested on strawberry plants in two production systems. UV-B administration was accompanied by concurrent red and blue light administration. Strawberry plants were young strawberry plants that were propagated using cutting methods and treated as runners. Two production systems were used: a hydroponic system and a soil system. The hydroponic system lacked soil and included liquid growth medium. The soil system included strawberry plants, grown from runners in pots.

Plants were grown for periods of time during which fruit was collected and assessed for various parameters. UV/light treatments were given for 14 days, using a UV/light photoperiod of 10 hours total. The photoperiod comprised cyclic, moving light treatments, carried out in a standard glasshouse.

For the hydroponic system, 10 plants were used for Experiment 1 and 10 plants were used Experiment 2. See Table 12 and Table 13. The Albion strawberry cultivar was used for Experiment 1, and the Monterey strawberry cultivar was used for Experiment 2. At the end of the trial period, the plants were harvested. Measurements were taken, as listed in Table 12 and in Table 13. The trial period lasted about 10 weeks. A total number of fruit that were harvested for each of Experiment 1 and Experiment 2 was more than 130 for each experiment. A total number of samples that were taken for each of Experiment 1 and for Experiment 2 was about 30 for each experiment. Data from Experiment 1 and Experiment 2 are shown in Table 12 and Table 13. A summary of percentage change for the different wavelengths for Experiment 1 and Experiment 2 is seen in Table 14.

TABLE 12

| Data from Hydroponic Experiment 1 | | | |
|---|---|---|---|
| | Control | UV 280 nm | UV 290 nm |
| Fruit fresh weight (FW) total (grams) | 2159.75 | 2309.66 | 2134.33 |
| Number of fruit harvested | 145.00 | 146.00 | 136.00 |
| Fruit FW average (grams) | 14.89 | 15.82 | 15.69 |
| % Fruit more than 16 grams | 33.79 | 38.36 | 39.71 |
| Brix average | 8.77 | 8.65 | 9.22 |
| % Fruit Brix 7 minimum | 83.33 | 86.30 | 94.12 |
| Width average (mm) | 28.90 | 30.24 | 29.85 |
| % Fruit width 25 mm minimum | 77.62 | 85.11 | 79.39 |
| Length average (mm) | 39.96 | 40.06 | 40.22 |
| % Min 25 mm, 7 brix | 65.52 | 69.86 | 73.53 |
| % Min 25 mm, 16 grams, brix 7 | 31.03 | 32.19 | 38.97 |
| Shoot FW average (grams) | 33.65 | 46.81 | 41.90 |

TABLE 12-continued

| Data from Hydroponic Experiment 1 | | | |
|---|---|---|---|
| | Control | UV 280 nm | UV 290 nm |
| Shoot dry weight (DW) average (grams) | 9.03 | 12.61 | 11.57 |
| Root DW average (grams) | 2.69 | 3.36 | 3.11 |
| Total DW average (grams) | 11.72 | 15.97 | 14.68 |
| Root/Shoot | 0.33 | 0.29 | 0.27 |
| Crown average | 2.20 | 2.80 | 2.90 |
| Leaf number average | 9.10 | 13.60 | 11.90 |
| Harvest Index | 2660.68 | 2079.70 | 2152.43 |

TABLE 13

Data from Hydroponic Experiment 2

|  | Control | UV 280 nm | UV 290 nm |
|---|---|---|---|
| Fruit fresh weight (FW) total (grams) | 1950.93 | 2019.68 | 2245.79 |
| Number of fruit harvested | 127.00 | 123.00 | 141.00 |
| Fruit FW average (grams) | 15.36 | 16.42 | 16.04 |
| % Fruit more than 16 grams | 42.52 | 47.97 | 43.97 |
| Brix average | 8.80 | 9.05 | 8.76 |
| % Fruit Brix 7 minimum | 85.04 | 93.50 | 87.94 |
| Width average (mm) | 30.79 | 31.67 | 30.99 |
| % Fruit width 25 mm minimum | 86.61 | 90.24 | 86.52 |
| Length average (mm) | 36.29 | 36.98 | 38.03 |
| % Min 25 mm, 7 brix | 74.80 | 84.55 | 78.72 |
| % Min 25 mm, 16 g, brix 7 | 37.01 | 47.15 | 41.84 |
| Shoot FW average (grams) | 39.16 | 59.29 | 56.72 |
| Shoot dry weight (DW) average (grams) | 10.42 | 12.74 | 12.80 |
| Root DW average (grans) | 2.51 | 2.74 | 2.73 |
| Total DW average (grams) | 12.93 | 15.48 | 15.52 |
| Root/Shoot | 0.25 | 0.24 | 0.23 |
| Crown average | 2.90 | 2.40 | 3.10 |
| Leaf number average | 12.00 | 11.44 | 14.00 |
| Harvest Index | 2293.35 | 1843.24 | 2116.40 |

TABLE 14

Summary of Hydroponic Data

| | Percentage change as compared to control for UV 280 (%) | | | Percentage change as compared to control for UV 290 (%) | | |
|---|---|---|---|---|---|---|
| | Experiment 1 | Experiment 2 | Average of Experiment 1 and Experiment 2 | Experiment 1 | Experiment 2 | Average of Experiment 1 and Experiment 2 |
| Fruit fresh weight (FW) total (grams) | 7 | 4 | 5 | −1 | 15 | 7 |
| Number of fruit harvested | 1 | −3 | −1 | −9 | 11 | 1 |
| Fruit FW average (grams) | 6 | 7 | 7 | 5 | 4 | 5 |
| % Fruit more than 16 grams | 14 | 13 | 13 | 17 | 3 | 10 |
| Brix average | −1 | 3 | 1 | 5 | 0 | 2 |
| % Fruit Brix 7 minimum | 4 | 10 | 7 | 13 | 3 | 8 |
| Width average (mm) | 5 | 3 | 4 | 3 | 1 | 2 |
| % Fruit width 25 mm minimum | 10 | 4 | 7 | 2 | 0 | 1 |
| Length average (mm) | 0 | 2 | 1 | 1 | 5 | 3 |
| % Min 25 mm, 7 brix | 7 | 13 | 10 | 12 | 5 | 9 |
| % Min 25 mm, 16 grams, brix 7 | 4 | 27 | 16 | 26 | 13 | 19 |
| Shoot FW average (grams) | 39 | 51 | 45 | 25 | 45 | 35 |
| Shoot dry weight (DW) average (grams) | 40 | 22 | 31 | 28 | 23 | 25 |
| Root DW average (g) | 25 | 9 | 17 | 16 | 9 | 12 |
| Total DW average (grams) | 36 | 20 | 28 | 25 | 20 | 23 |

TABLE 14-continued

Summary of Hydroponic Data

| | Percentage change as compared to control for UV 280 (%) | | | Percentage change as compared to control for UV 290 (%) | | |
|---|---|---|---|---|---|---|
| | Experiment 1 | Experiment 2 | Average of Experiment 1 and Experiment 2 | Experiment 1 | Experiment 2 | Average of Experiment 1 and Experiment 2 |
| Root/Shoot | −11 | −6 | −8 | −16 | −9 | −12 |
| Crown average | 27 | −17 | 5 | 32 | 7 | 19 |
| Leaf number average | 49 | −5 | 22 | 31 | 17 | 24 |
| Harvest Index | −22 | −20 | −21 | −19 | −8 | −13 |

These results indicate that UV administration positively affected plant growth and fruit production, consistent with the disclosure herein if UV-B treatment increasing both plant yield and plant hardiness.

For the soil systems, the Camarosa strawberry cultivar was used. A total of 15 plants were used. At the end of the trial period, the plants were harvested and measured as indicated in Table 15. The trial period lasted about 12 weeks. Samples were harvested during multiple time points during the trial period. There were 28 time points and a number of fruit that were sampled per time point was less than 40. Data from the experiment is shown in Table 15. A summary of percentage change for the experiment is seen in Table 16 and FIG. 2.

TYABLE 15

Data from Soil System

| | Control | UV 280 nm |
|---|---|---|
| Fruit fresh weight (FW) total (grams) | 9361.8 | 12553.5 |
| Number of fruit harvested | 445.0 | 608.0 |
| Fruit FW average (grams) | 21.0 | 20.6 |
| Fruit FW average more than 16 grams | 25.6 | 26.1 |
| % Fruit more than 16 grams | 68.8 | 63.7 |
| Brix average | 7.9 | 8.0 |
| Shoot FW average (grams) | 414.7 | 481.8 |
| Shoot dry weight (DW) average (grams) | 99.1 | 125.0 |
| Harvest Index | 712.7 | 709.2 |

TABLE 16

Summary of Soil System Data

| | Percentage change as compared to control for UV 280 (%) |
|---|---|
| Fruit fresh weight (FW) total (grams) | 34.1 |
| Number of fruit harvested | 36.6 |
| Fruit FW average (grams) | −1.9 |
| Fruit FW average more than 16 grams | 2.2 |
| % Fruit more than 16 grams | −7.4 |
| Brix average | 1.3 |

TABLE 16-continued

Summary of Soil System Data

| | Percentage change as compared to control for UV 280 (%) |
|---|---|
| Shoot FW average (grams) | 16.2 |
| Shoot dry weight (DW) average (grams) | 26.1 |
| Harvest Index | −0.5 |

Data from the hydroponic system showed that fruit fresh weight (FW), percentage of fruit more than 16 grams in weight, percentage of fruit with Brix average greater than 7 (% Fruit Brix 7 minimum), percentage of fruit with fruit diameter greater than 25 mm with Brix of 7, percentage of fruit with fruit diameter greater than 25 mm with Brix of 7, and fresh weight greater than 16 grams were increased following UV-B treatment of 280 nm and 290 nm as compared to control.

Figure 2:
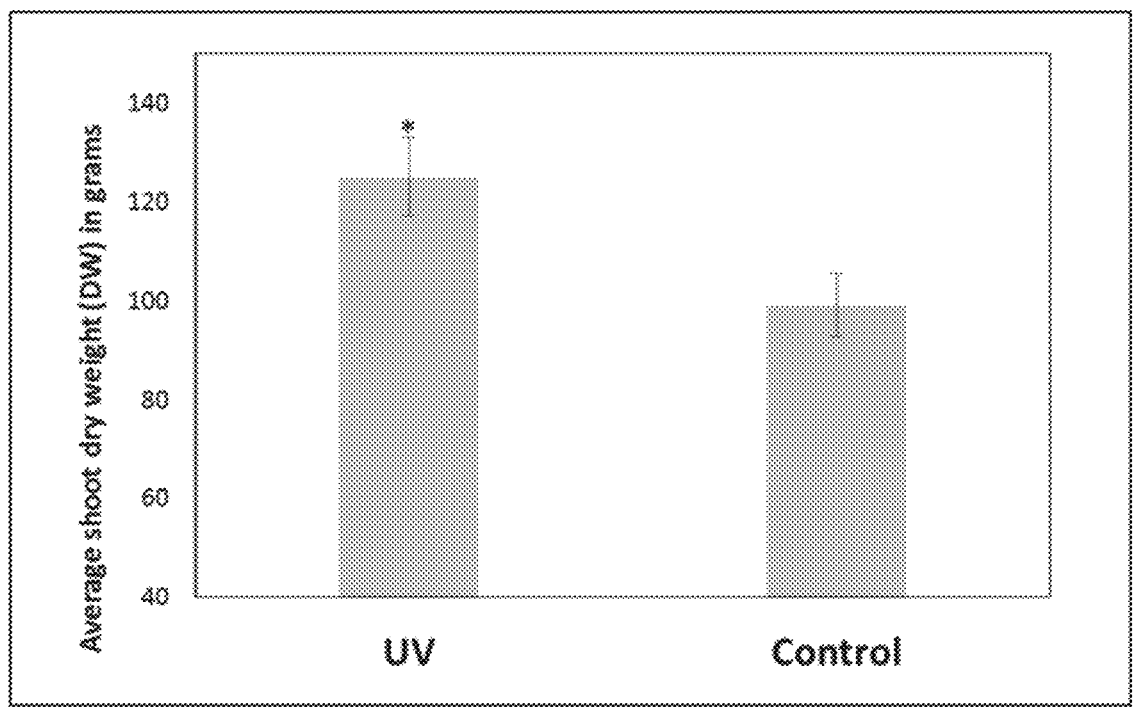
FIG. 2 depicts a graph of average shoot dry weight (DW) in control and after UV-B radiation of 280 nm of strawberry cultivar.

Data from the soil system showed that there was a significant increase ($p \leq 0.05$) in the number of fruit harvested per plant. There was also a significant increase in plant biomass of about 26% as measured as dry weight (FIG. 2).

This example demonstrates that improved strawberry parameters of productivity are attained in soil grown and hydroponically grown strawberry populations following UV-B radiation. These results indicate that UV administration positively affected plant growth and fruit production, consistent with the disclosure herein if UV-B treatment increasing both plant yield and plant hardiness.

This example supports that UV seed treatment provides protection against yield-limiting stresses encountered in the growing environment, such as drought or salinity stress, and that the advantages of the disclosure can be achieved by using a treatment at different wavelengths within the UV-B waveband.

Example 9—Treatment Regimens

Exemplary treatment recipes are seen in Tables 17-27.

TABLE 17

Recipe 1

| Recipe variable | Inner ranges | Outer ranges |
|---|---|---|
| Treatment distance from plant to light source (mm) | 30 to 120 | <10, >200 |
| Speed of moving light source (mm/second) | 40 to 60 | <20, >100 |
| Light source timing cycles (regularity of each exposure, seconds) | 90 to 180 | <20, >300 |
| Number of cycles per day | 380 to 500 | <250, >600 |
| Irradiance of UV-B (umol cm_HU $-2$ s$^{-1}$) | 15 to 40 | <15, >80 |
| Peak wavelength of UV-B | 280 to 300 | <279, >305 |
| Irradiance of red light (umol m$^{-2}$ s$^{-1}$) | 66 to 266 | <30, >3000 |
| Peak wavelength of red light (nm) | 640 to 680 | <620, >690 |
| Irradiance of blue light (umol m$^2$ s$^{-1}$) | 33 to 133 | <5, >2000 |
| Peak wavelength of blue light (nm) | 440-460 | <430, >480 |
| Total days of treatment | 5 to 20 | <2, >30 |

TABLE 18

Recipe 2

| Recipe variable | Value |
|---|---|
| Treatment distance from plant to light source (mm) | 90 |
| Speed of moving light source (mm/second) | 53 |
| Light source timing cycles (regularity of each exposure, seconds) | 169 |
| Number of cycles per day | 433 |
| Irradiance of UV-B (umol cm$^{-2}$ s$^{-1}$) | 20 |
| Peak wavelength of UV-B | 283 |
| Irradiance of red light (umol m$^{-2}$ s$^{-1}$) | 133 |
| Peak wavelength of red light (nm) | 659 |
| Irradiance of blue light (umol m$^{-2}$ s$^{-1}$) | 66 |
| Peak wavelength of blue light (nm) | 443 |
| Total days of treatment | 12 |

TABLE 19

Recipe 3

| Recipe variable | Value |
|---|---|
| Treatment distance from plant to light source (mm) | 70 |
| Speed of moving light source (mm/second) | 45 |
| Light source timing cycles (regularity of each exposure, seconds) | 133 |
| Number of cycles per day | 383 |
| Irradiance of UV-B (umol cm$^{-2}$ s$^{-1}$) | 15 |
| Peak wavelength of UV-B | 286 |
| Irradiance of red light (umol m$^{-2}$ s$^{-1}$) | 133 |
| Peak wavelength of red light (nm) | 659 |
| Irradiance of blue light (umol m$^{-2}$ s$^{-1}$) | 55 |
| Peak wavelength of blue light (nm) | 443 |
| Total days of treatment | 14 |

TABLE 20

Recipe 4

| Recipe variable | Value |
|---|---|
| Treatment distance from plant to light source (mm) | 120 |
| Speed of moving light source (mm/second) | 60 |
| Light source timing cycles (regularity of each exposure, seconds) | 133 |
| Number of cycles per day | 493 |
| Irradiance of UV-B (umol cm$^{-2}$ s$^{-1}$) | 23 |
| Peak wavelength of UV-B | 281 |
| Irradiance of red light (umol m$^{-2}$ s$^{-1}$) | 233 |
| Peak wavelength of red light (nm) | 659 |
| Irradiance of blue light (umol m$^{-2}$ s$^{-1}$) | 66 |
| Peak wavelength of blue light (nm) | 453 |
| Total days of treatment | 10 |

TABLE 21

Recipe 5

| Recipe variable | Value |
|---|---|
| Treatment distance from plant to light source (mm) | 30 |
| Speed of moving light source (mm/second) | 40 |
| Light source timing cycles (regularity of each exposure, seconds) | 93 |
| Number of cycles per day | 433 |
| Irradiance of UV-B (umol cm$^{-2}$ s$^{-1}$) | 20 |
| Peak wavelength of UV-B | 282 |
| Irradiance of red light (umol m$^{-2}$ s$^{-1}$) | 77 |
| Peak wavelength of red light (nm) | 643 |
| Irradiance of blue light (umol m$^{-2}$ s$^{-1}$) | 66 |
| Peak wavelength of blue light (nm) | 443 |
| Total days of treatment | 14 |

TABLE 22

Recipe 6

| Recipe variable | Value |
|---|---|
| Treatment distance from plant to light source (mm) | 70 |
| Speed of moving light source (mm/second) | 53 |
| Light source timing cycles (regularity of each exposure, seconds) | 133 |
| Number of cycles per day | 433 |
| Irradiance of UV-B (umol cm$^{-2}$ s$^{-1}$) | 20 |
| Peak wavelength of UV-B | 282 |
| Irradiance of red light (umol m$^{-2}$ s$^{-1}$) | 133 |
| Peak wavelength of red light (nm) | 659 |
| Irradiance of blue light (umol m$^{-2}$ s$^{-1}$) | 66 |
| Peak wavelength of blue light (nm) | 453 |
| Total days of treatment | 14 |

TABLE 23

Recipe 7

| Recipe variable | Value |
|---|---|
| Treatment distance from plant to light source (mm) | 70 |
| Speed of moving light source (mm/second) | 57 |
| Light source timing cycles (regularity of each exposure, seconds) | 133 |
| Number of cycles per day | 393 |
| Irradiance of UV-B (umol cm$^{-2}$ s$^{-1}$) | 18 |
| Peak wavelength of UV-B | 286 |
| Irradiance of red light (umol m$^{-2}$ s$^{-1}$) | 144 |
| Peak wavelength of red light (nm) | 659 |
| Irradiance of blue light (umol m$^{-2}$ s$^{-1}$) | 88 |
| Peak wavelength of blue light (nm) | 460 |
| Total days of treatment | 14 |

TABLE 24

Recipe 8

| Recipe variable | Value |
| --- | --- |
| Treatment distance from plant to light source (mm) | 120 |
| Speed of moving light source (mm/second) | 53 |
| Light source timing cycles (regularity of each exposure, seconds) | 133 |
| Number of cycles per day | 480 |
| Irradiance of UV-B (umol cm$^{-2}$ s$^{-1}$) | 15 |
| Peak wavelength of UV-B | 282 |
| Irradiance of red light (umol m$^{-2}$ s$^{-1}$) | 144 |
| Peak wavelength of red light (nm) | 659 |
| Irradiance of blue light (umol m$^{-2}$ s$^{-1}$) | 112 |
| Peak wavelength of blue light (nm) | 440 |
| Total days of treatment | 5 |

TABLE 25

Recipe 9

| Recipe variable | Value |
| --- | --- |
| Treatment distance from plant to light source (mm) | 80 |
| Speed of moving light source (mm/second) | 43 |
| Light source timing cycles (regularity of each exposure, seconds) | 133 |
| Number of cycles per day | 383 |
| Irradiance of UV-B (umol cm$^{-2}$ s$^{-1}$) | 30 |
| Peak wavelength of UV-B | 294 |
| Irradiance of red light (umol m$^{-2}$ s$^{-1}$) | 163 |
| Peak wavelength of red light (nm) | 659 |
| Irradiance of blue light (umol m$^{-2}$ s$^{-1}$) | 88 |
| Peak wavelength of blue light (nm) | 440-460 |
| Total days of treatment | 8 |

TABLE 26

Recipe 10

| Recipe variable | Value |
| --- | --- |
| Treatment distance from plant to light source (mm) | 70 |
| Speed of moving light source (mm/second) | 53 |
| Light source timing cycles (regularity of each exposure, seconds) | 133 |
| Number of cycles per day | 433 |
| Irradiance of UV-B (umol cm$^{-2}$ s$^{-1}$) | 30 |
| Peak wavelength of UV-B | 292 |
| Irradiance of red light (umol m$^{-2}$ s$^{-1}$) | 133 |
| Peak wavelength of red light (nm) | 659 |
| Irradiance of blue light (umol m$^{-2}$ s$^{-1}$) | 66 |
| Peak wavelength of blue light (nm) | 440-460 |
| Total days of treatment | 14 |

TABLE 27

Recipe 11

| Recipe variable | Value |
| --- | --- |
| Treatment distance from plant to light source (mm) | 70 |
| Speed of moving light source (mm/second) | 60 |

TABLE 27-continued

Recipe 11

| Recipe variable | Value |
| --- | --- |
| Light source timing cycles (regularity of each exposure, seconds) | 90 |
| Number of cycles per day | 380 |
| Irradiance of UV-B (umol cm$^{-2}$ s$^{-1}$) | 20 |
| Peak wavelength of UV-B | 300 |
| Irradiance of red light (umol m$^{-2}$ s$^{-1}$) | 133 |
| Peak wavelength of red light (nm) | 640 |
| Irradiance of blue light (umol m$^{-2}$ s$^{-1}$) | 66 |
| Peak wavelength of blue light (nm) | 440-460 |
| Total days of treatment | 14 |

Aspects of the present disclosure have been described by way of example only and it should be appreciated that modifications and additions may be made thereto without departing from the scope of the appended claims.

What I claim is:

1. A method for increasing yield of a flowering part of a *cannabis* plant, comprising: subjecting a plant material prior to flower emergence to a treatment regimen comprising:
    a) light comprising at least one UV wavelength in a range from 280 nm to 295 nm;
    b) a duration between about 6 days and about 14 days wherein the plant material is not a seed, and wherein the yield in the flowering part of the *cannabis* plant is improved by at least 5% as compared to an untreated *cannabis* plant wherein the untreated *cannabis* plant is not under biotic environmental stress.

2. The method of claim 1, wherein the at least one UV wavelength is peaking at least one of 280 nm, 282 nm, 285 nm, 287 nm, 291 nm, and 292 nm.

3. The method of claim 1, wherein the plant material is at least one of a seedling and a cutting.

4. The method of claim 1, wherein an irradiance of the UV-B wavelength is in a range of $4 \times 10^{-5}$ W cm$^{-2}$s$^{-1}$ to $1.3 \times 10^{-4}$ W cm$^{-2}$s$^{-1}$.

5. The method of claim 1, wherein the light comprises a wavelength of blue light in a range of about 440 nm to about 460 nm.

6. The method of claim 1, wherein the light comprises a wavelength of red light in a range of about 640 nm to about 680 nm.

7. The method of claim 1, wherein the light comprises a wavelength of blue light in a range of about 440 nm to about 460 nm, and a wavelength of red light in a range of about 640 nm to about 680 nm.

8. The method of claim 1, wherein the light is administered indoors.

9. The method of claim 1, wherein the number of cycles per day in a range of about 100 to about 500 cycles per day.

10. The method of claim 1, wherein the UV wavelength is not administered to the fruiting component.

11. The method of claim 1, wherein the UV-B treatment results in an improved long-term hardiness.

* * * * *